(12) United States Patent
Jackson

(10) Patent No.: US 8,377,067 B2
(45) Date of Patent: *Feb. 19, 2013

(54) ORTHOPEDIC IMPLANT ROD REDUCTION TOOL SET AND METHOD

(76) Inventor: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/374,932

(22) Filed: Jan. 24, 2012

(65) Prior Publication Data

US 2012/0158070 A1    Jun. 21, 2012

Related U.S. Application Data

(60) Continuation of application No. 12/584,413, filed on Sep. 4, 2009, now Pat. No. 8,100,915, which is a continuation of application No. 12/220,185, filed on Jul. 22, 2008, now Pat. No. 8,162,948, which is a division of application No. 10/789,149, filed on Feb. 27, 2004, now Pat. No. 7,160,300.

(51) Int. Cl.
    *A61B 17/86*       (2006.01)
    *A61B 17/90*       (2006.01)

(52) U.S. Cl. ...................... 606/86 A; 606/305

(58) Field of Classification Search ............. 606/86 A, 606/305, 914, 264, 279, 104, 90, 99, 205–208
See application file for complete search history.

(56) References Cited

U.S. PATENT DOCUMENTS

| | | |
|---|---|---|
| 854,956 A | 5/1907 | Martin |
| 1,472,464 A | 10/1923 | Ellison |
| 2,243,717 A | 5/1941 | Moreira |
| 2,346,346 A | 4/1944 | Anderson |
| 2,362,999 A | 11/1944 | Elmer |
| 2,524,095 A | 10/1950 | Williams |
| 2,531,892 A | 11/1950 | Reese |
| 2,532,972 A | 12/1950 | Vertin |
| 2,579,438 A | 12/1951 | Longfellow |
| 2,669,896 A | 2/1954 | Clough |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 4,033,139 A | 7/1977 | Frederick |
| 4,041,939 A | 8/1977 | Hall |

(Continued)

FOREIGN PATENT DOCUMENTS

| | | |
|---|---|---|
| CA | 2577436 | 6/2006 |
| DE | 9202745.8 | 4/1992 |

(Continued)

OTHER PUBLICATIONS

Brochure of Spinal Concepts, *Pathfinder, Minimally Invasive Pedicle Fixation System*, Publication Date: May 2003.

(Continued)

*Primary Examiner* — Pedro Philogene
(74) *Attorney, Agent, or Firm* — John C. McMahon

(57) ABSTRACT

A tool set for implanting a rod in a human spine in conjunction with bone screws. The tool set includes a pair of end guide tools that receive opposite ends of the rod in channels and under manipulation by a surgeon facilitate transport of the rod toward the bone screws attached to the guide tools. Intermediate guide tools having guiding pass through slots are utilized to guide intermediate locations along the rod toward associated bone screws. An attachment structure operably connects the guide tools to the bone screws. The guide tools each include a lower guide and advancement structure to allow a closure top with mating structure to be rotated and driven downward against the rod and to cooperate with similar structure in the bone screw to seat and lock the rod therein.

14 Claims, 13 Drawing Sheets

U.S. PATENT DOCUMENTS

| | | |
|---|---|---|
| 4,190,091 A | 2/1980 | Colognori |
| 4,347,845 A | 9/1982 | Mayfield |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,877,020 A | 10/1989 | Vich |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,015,247 A | 5/1991 | Michelson |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,067,955 A | 11/1991 | Cotrel |
| 5,084,048 A | 1/1992 | Jacob et al. |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Baker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,346,493 A | 9/1994 | Stahurski et al. |
| 5,354,292 A | 10/1994 | Braeuer et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,392 A | 11/1997 | Richelsoph |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |

| | | | | | | |
|---|---|---|---|---|---|---|
| 6,063,088 | A | 5/2000 | Winslow | 6,540,749 B2 | 4/2003 | Schafer et al. |
| 6,063,090 | A | 5/2000 | Schlapfer | 6,547,790 B2 | 4/2003 | Harkey, III et al. |
| 6,074,391 | A | 6/2000 | Metz-Stavenhagen et al. | 6,551,320 B2 | 4/2003 | Liebermann |
| 6,077,262 | A | 6/2000 | Schlapfer et al. | 6,551,323 B2 | 4/2003 | Doubler et al. |
| 6,086,588 | A | 7/2000 | Ameil et al. | 6,554,831 B1 | 4/2003 | Rivard et al. |
| 6,090,110 | A | 7/2000 | Metz-Stavenhagen | 6,554,832 B2 | 4/2003 | Shluzas |
| 6,090,111 | A | 7/2000 | Nichols | 6,554,834 B1 | 4/2003 | Crozet et al. |
| 6,099,528 | A | 8/2000 | Saurat | 6,558,387 B2 | 5/2003 | Errico et al. |
| 6,102,912 | A | 8/2000 | Cazin et al. | 6,562,038 B1 | 5/2003 | Morrison |
| 6,102,913 | A | 8/2000 | Jackson | 6,562,040 B1 | 5/2003 | Wagner |
| 6,110,172 | A | 8/2000 | Jackson | 6,565,565 B1 | 5/2003 | Yuan et al. |
| 6,113,601 | A | 9/2000 | Tatar | 6,565,567 B1 | 5/2003 | Haider |
| 6,117,137 | A | 9/2000 | Halm et al. | 6,572,618 B1 | 6/2003 | Morrison |
| 6,132,431 | A | 10/2000 | Nilsson et al. | 6,582,436 B2 | 6/2003 | Schlapfer et al. |
| 6,132,432 | A | 10/2000 | Richelsoph | 6,582,466 B1 | 6/2003 | Gauchet |
| 6,132,434 | A | 10/2000 | Sherman et al. | 6,585,740 B2 | 7/2003 | Schlapfer et al. |
| 6,136,002 | A | 10/2000 | Shih et al. | 6,595,992 B1 | 7/2003 | Wagner et al. |
| 6,139,549 | A | 10/2000 | Keller | 6,595,993 B2 | 7/2003 | Donno et al. |
| 6,143,032 | A | 11/2000 | Schafer et al. | 6,599,294 B2 | 7/2003 | Fuss et al. |
| 6,146,383 | A | 11/2000 | Studer et al. | 6,610,063 B2 | 8/2003 | Kumar et al. |
| 6,183,472 | B1 | 2/2001 | Lutz | 6,613,050 B1 | 9/2003 | Wagner et al. |
| 6,186,718 | B1 | 2/2001 | Fogard | 6,616,667 B1 | 9/2003 | Steiger et al. |
| 6,187,005 | B1 | 2/2001 | Brace et al. | 6,616,669 B2 | 9/2003 | Ogilvie et al. |
| 6,189,422 | B1 | 2/2001 | Stihl | 6,623,485 B2 | 9/2003 | Doubler et al. |
| 6,193,720 | B1 | 2/2001 | Yuan et al. | 6,626,347 B2 | 9/2003 | Ng |
| 6,214,012 | B1 | 4/2001 | Karpman et al. | 6,626,907 B2 | 9/2003 | Campbell et al. |
| RE37,161 | E | 5/2001 | Michelson et al. | 6,626,908 B2 | 9/2003 | Cooper et al. |
| 6,224,596 | B1 | 5/2001 | Jackson | 6,635,059 B2 | 10/2003 | Randall et al. |
| 6,224,598 | B1 | 5/2001 | Jackson | 6,635,060 B2 | 10/2003 | Hanson et al. |
| 6,235,028 | B1 | 5/2001 | Brumfield et al. | 6,648,885 B1 | 11/2003 | Friesem |
| 6,235,034 | B1 | 5/2001 | Bray | 6,648,887 B2 | 11/2003 | Ashman |
| 6,241,730 | B1 | 6/2001 | Alby | 6,648,888 B1 | 11/2003 | Shluzas |
| 6,248,105 | B1 | 6/2001 | Schlapfer et al. | 6,652,526 B1 | 11/2003 | Arafiles |
| 6,248,107 | B1 | 6/2001 | Foley et al. | 6,652,765 B1 | 11/2003 | Beaty |
| 6,251,112 | B1 | 6/2001 | Jackson | 6,656,179 B1 | 12/2003 | Schaefer et al. |
| 6,254,146 | B1 | 7/2001 | Church | 6,656,181 B2 | 12/2003 | Dixon et al. |
| 6,254,602 | B1 | 7/2001 | Justis | 6,660,004 B2 | 12/2003 | Barker et al. |
| 6,267,764 | B1 | 7/2001 | Elberg | 6,660,006 B2 | 12/2003 | Markworth et al. |
| 6,267,765 | B1 | 7/2001 | Taylor et al. | 6,663,632 B1 | 12/2003 | Frigg |
| 6,273,888 | B1 | 8/2001 | Justis | 6,663,635 B2 | 12/2003 | Frigg et al. |
| 6,277,122 | B1 | 8/2001 | McGahan et al. | 6,673,073 B1 | 1/2004 | Schafer |
| 6,280,442 | B1 | 8/2001 | Barker et al. | 6,676,661 B1 | 1/2004 | Martin Benlloch et al. |
| 6,280,445 | B1 | 8/2001 | Morrison et al. | 6,679,833 B2 | 1/2004 | Smith et al. |
| 6,287,308 | B1 | 9/2001 | Betz et al. | 6,682,529 B2 | 1/2004 | Stahurski |
| 6,287,311 | B1 | 9/2001 | Sherman et al. | 6,682,530 B2 | 1/2004 | Dixon et al. |
| 6,290,700 | B1 | 9/2001 | Schmotzer | 6,689,133 B2 | 2/2004 | Morrison et al. |
| 6,296,642 | B1 | 10/2001 | Morrison et al. | 6,689,134 B2 | 2/2004 | Ralph et al. |
| 6,296,643 | B1 | 10/2001 | Hopf et al. | 6,695,843 B2 | 2/2004 | Biedermann et al. |
| 6,299,613 | B1 | 10/2001 | Ogilvie et al. | 6,695,851 B2 | 2/2004 | Zdeblick et al. |
| 6,299,616 | B1 | 10/2001 | Berger | 6,699,249 B2 | 3/2004 | Schlapfer et al. |
| 6,302,888 | B1 | 10/2001 | Mellinger et al. | 6,706,045 B2 | 3/2004 | Lin et al. |
| 6,309,391 | B1 | 10/2001 | Crandall et al. | 6,712,818 B1 | 3/2004 | Michelson |
| 6,315,564 | B1 | 11/2001 | Levisman | 6,716,213 B2 | 4/2004 | Shitoto |
| 6,315,779 | B1 | 11/2001 | Morrison et al. | 6,716,214 B1 | 4/2004 | Jackson |
| 6,331,179 | B1 | 12/2001 | Freid et al. | 6,716,247 B2 | 4/2004 | Michelson |
| 6,355,040 | B1 | 3/2002 | Richelsoph et al. | 6,723,100 B2 | 4/2004 | Bieeermann et al. |
| RE37,665 | E | 4/2002 | Ralph et al. | 6,730,093 B2 | 5/2004 | Saint Martin |
| 6,368,321 | B1 | 4/2002 | Jackson | 6,730,127 B2 | 5/2004 | Michelson |
| 6,371,957 | B1 | 4/2002 | Amrein et al. | 6,733,502 B2 | 5/2004 | Altarac et al. |
| 6,402,752 | B2 | 6/2002 | Schaffler-Wachter et al. | 6,736,816 B2 | 5/2004 | Ritland |
| 6,402,757 | B1 | 6/2002 | Moore et al. | 6,736,820 B2 | 5/2004 | Biedermann et al. |
| 6,440,133 | B1 | 8/2002 | Beale et al. | 6,740,086 B2 | 5/2004 | Richelsoph |
| 6,440,137 | B1 | 8/2002 | Horvath et al. | 6,740,089 B2 | 5/2004 | Haider |
| 6,443,956 | B1 | 9/2002 | Ray | 6,743,231 B1 | 6/2004 | Gray |
| 6,451,021 | B1 | 9/2002 | Ralph et al. | 6,746,449 B2 | 6/2004 | Jones et al. |
| 6,471,703 | B1 | 10/2002 | Ashman | 6,746,454 B2 | 6/2004 | Winterbottom et al. |
| 6,471,705 | B1 | 10/2002 | Biedermann et al. | 6,755,829 B1 | 6/2004 | Bono et al. |
| 6,478,801 | B1 | 11/2002 | Ralph et al. | 6,755,835 B2 | 6/2004 | Schultheiss et al. |
| 6,485,491 | B1 | 11/2002 | Farris et al. | 6,755,836 B1 | 6/2004 | Lewis |
| 6,485,492 | B1 | 11/2002 | Halm et al. | 6,761,723 B2 | 7/2004 | Butterman et al. |
| 6,485,494 | B1 | 11/2002 | Haider | 6,767,351 B2 | 7/2004 | Orbay et al. |
| 6,488,681 | B2 | 12/2002 | Martin et al. | 6,770,075 B2 | 8/2004 | Howland |
| 6,508,818 | B2 | 1/2003 | Steiner et al. | 6,778,861 B1 | 8/2004 | Liebrecht et al. |
| 6,511,484 | B2 | 1/2003 | Torode et al. | 6,780,186 B2 | 8/2004 | Errico et al. |
| 6,520,962 | B1 | 2/2003 | Taylor et al. | 6,783,527 B2 | 8/2004 | Drewry et al. |
| 6,527,804 | B1 | 3/2003 | Gauchet et al. | 6,790,208 B2 | 9/2004 | Oribe et al. |
| 6,530,929 | B1 | 3/2003 | Justis et al. | 6,790,209 B2 | 9/2004 | Beale et al. |
| 6,533,786 | B1 | 3/2003 | Needham et al. | 6,802,844 B2 | 10/2004 | Ferree |
| 6,539,826 | B2 | 4/2003 | Oesterle et al. | 6,827,719 B2 | 12/2004 | Ralph et al. |

| | | | | | | |
|---|---|---|---|---|---|---|
| 6,830,571 B2 | 12/2004 | Lenke et al. | | 7,306,603 B2 | 12/2007 | Boehm et al. |
| 6,835,196 B2 | 12/2004 | Biedermann et al. | | 7,306,604 B2 | 12/2007 | Carli |
| 6,837,889 B2 | 1/2005 | Shluzas | | 7,306,606 B2 | 12/2007 | Sasing |
| 6,840,940 B2 | 1/2005 | Ralph et al. | | 7,314,467 B2 | 1/2008 | Howland |
| 6,843,791 B2 | 1/2005 | Serhan | | 7,316,684 B1 | 1/2008 | Baccelli et al. |
| 6,857,343 B1 | 2/2005 | Easterbrooks et al. | | 7,322,979 B2 | 1/2008 | Crandall et al. |
| 6,858,031 B2 | 2/2005 | Morrison et al. | | 7,329,258 B2 | 2/2008 | Studer |
| 6,869,432 B2 | 3/2005 | Schlapfer et al. | | 7,335,201 B2 | 2/2008 | Doubler et al. |
| 6,869,433 B2 | 3/2005 | Glascott | | 7,335,202 B2 | 2/2008 | Matthis et al. |
| 6,872,208 B1 | 3/2005 | McBride et al. | | 7,338,490 B2 | 3/2008 | Ogilvie et al. |
| 6,896,676 B2 | 5/2005 | Zubok et al. | | 7,338,491 B2 | 3/2008 | Baker et al. |
| 6,896,677 B1 | 5/2005 | Lin | | 7,361,196 B2 | 4/2008 | Fallin et al. |
| 6,932,817 B2 | 8/2005 | Baynham et al. | | 7,377,921 B2 | 5/2008 | Studer et al. |
| 6,932,820 B2 | 8/2005 | Osman | | 7,445,627 B2 | 11/2008 | Hawkes et al. |
| 6,945,972 B2 | 9/2005 | Frigg et al. | | 7,465,306 B2 | 12/2008 | Pond |
| 6,953,462 B2 | 10/2005 | Lieberman | | 7,470,279 B2 | 12/2008 | Jackson |
| 6,955,677 B2 | 10/2005 | Dahners | | 7,476,228 B2 | 1/2009 | Abdou |
| 6,958,065 B2 | 10/2005 | Ueyama et al. | | 7,476,238 B2 | 1/2009 | Panjabi |
| 6,964,664 B2 | 11/2005 | Freid et al. | | 7,479,156 B2 | 1/2009 | Lourdel et al. |
| 6,964,665 B2 | 11/2005 | Thomas et al. | | 7,491,208 B2 | 2/2009 | Pond, Jr. et al. |
| 6,964,667 B2 | 11/2005 | Shaolian et al. | | 7,491,218 B2 | 2/2009 | Landry et al. |
| 6,966,910 B2 | 11/2005 | Ritland | | 7,491,221 B2 | 2/2009 | David |
| 6,974,460 B2 | 12/2005 | Carbone et al. | | 7,503,918 B2 | 3/2009 | Baccelli et al. |
| 6,979,334 B2 | 12/2005 | Dalton | | 7,503,924 B2 | 3/2009 | Lee et al. |
| 6,981,973 B2 | 1/2006 | McKinley | | 7,524,323 B2 | 4/2009 | Malandain |
| 6,986,771 B2 | 1/2006 | Paul et al. | | 7,527,640 B2 | 5/2009 | Ziolo et al. |
| 6,989,011 B2 | 1/2006 | Paul et al. | | 7,530,992 B2 | 5/2009 | Biedermann et al. |
| 6,991,632 B2 | 1/2006 | Ritland | | 7,556,639 B2 | 7/2009 | Rothman et al. |
| 7,004,947 B2 | 2/2006 | Shluzas et al. | | 7,559,942 B2 | 7/2009 | Paul et al. |
| RE39,035 E | 3/2006 | Finn et al. | | 7,559,943 B2 | 7/2009 | Mujwid |
| 7,008,422 B2 | 3/2006 | Foley et al. | | 7,563,274 B2 | 7/2009 | Justis et al. |
| 7,008,424 B2 | 3/2006 | Teitelbaum | | 7,563,275 B2 | 7/2009 | Falahee et al. |
| 7,011,660 B2 | 3/2006 | Sherman et al. | | 7,563,283 B2 | 7/2009 | Kwak |
| 7,018,378 B2 | 3/2006 | Biedermann et al. | | 7,569,061 B2 | 8/2009 | Colleran |
| 7,018,379 B2 | 3/2006 | Drewry et al. | | 7,572,279 B2 | 8/2009 | Jackson |
| 7,022,122 B2 | 4/2006 | Amrein et al. | | 7,572,280 B2 | 8/2009 | Dickinson et al. |
| 7,029,475 B2 | 4/2006 | Panjabi | | 7,575,587 B2 | 8/2009 | Rezach et al. |
| RE39,089 E | 5/2006 | Ralph et al. | | 7,588,575 B2 | 9/2009 | Colleran et al. |
| 7,052,497 B2 | 5/2006 | Sherman et al. | | 7,588,588 B2 | 9/2009 | Spitler et al. |
| 7,056,321 B2 | 6/2006 | Pagliuca et al. | | 7,588,589 B2 | 9/2009 | Falahee |
| 7,066,062 B2 | 6/2006 | Flesher | | 7,588,593 B2 | 9/2009 | Aferzon |
| 7,066,937 B2 | 6/2006 | Shluzas | | 7,591,839 B2 | 9/2009 | Biedermann et al. |
| 7,081,116 B1 | 7/2006 | Carly | | 7,601,166 B2 | 10/2009 | Biedermann et al. |
| 7,083,621 B2 | 8/2006 | Shaolian et al. | | 7,604,653 B2 | 10/2009 | Kitchen |
| 7,087,057 B2 | 8/2006 | Konieczynski et al. | | 7,604,654 B2 | 10/2009 | Fallin et al. |
| 7,090,674 B2 | 8/2006 | Doubler et al. | | 7,604,655 B2 | 10/2009 | Warnick |
| 7,090,679 B2 | 8/2006 | Saint-Martin et al. | | 7,604,656 B2 | 10/2009 | Shluzas |
| 7,090,680 B2 | 8/2006 | Bonati et al. | | 7,611,518 B2 | 11/2009 | Walder et al. |
| 7,094,242 B2 | 8/2006 | Ralph et al. | | 7,615,068 B2 | 11/2009 | Timm et al. |
| 7,118,576 B2 | 10/2006 | Gitis et al. | | 7,618,442 B2 | 11/2009 | Spitler |
| 7,121,755 B2 | 10/2006 | Schlapfer et al. | | 7,621,912 B2 | 11/2009 | Harms et al. |
| 7,125,410 B2 | 10/2006 | Freudiger | | 7,621,940 B2 | 11/2009 | Harms et al. |
| 7,125,426 B2 | 10/2006 | Moumene et al. | | 7,621,941 B2 | 11/2009 | Schlapfer et al. |
| 7,128,743 B2 | 10/2006 | Metz-Stavenhagen | | 7,625,393 B2 | 12/2009 | Fallin et al. |
| 7,137,985 B2 | 11/2006 | Jahng | | 7,625,394 B2 | 12/2009 | Molz, IV et al. |
| 7,141,051 B2 | 11/2006 | Janowski et al. | | 7,632,292 B2 | 12/2009 | Sengupta et al. |
| 7,144,396 B2 | 12/2006 | Shluzas | | 7,641,673 B2 | 1/2010 | LeCouedic et al. |
| 7,160,300 B2 * | 1/2007 | Jackson .................. 606/273 | | 7,641,674 B2 | 1/2010 | Young |
| 7,163,538 B2 | 1/2007 | Altarac et al. | | 7,645,294 B2 | 1/2010 | Kalfas et al. |
| 7,163,539 B2 | 1/2007 | Abdelgany et al. | | 7,648,522 B2 | 1/2010 | David |
| 7,166,108 B2 | 1/2007 | Mazda et al. | | 7,651,515 B2 | 1/2010 | Mack et al. |
| 7,179,261 B2 | 2/2007 | Sicvol et al. | | 7,655,026 B2 | 2/2010 | Justis et al. |
| 7,186,255 B2 | 3/2007 | Baynham et al. | | 7,658,739 B2 | 2/2010 | Shluzas |
| 7,188,626 B2 | 3/2007 | Foley et al. | | 7,658,752 B2 | 2/2010 | Labrom et al. |
| 7,207,991 B2 | 4/2007 | Michelson | | 7,666,188 B2 | 2/2010 | Anderson |
| 7,207,992 B2 | 4/2007 | Ritland | | 7,674,277 B2 | 3/2010 | Burd et al. |
| 7,211,085 B2 | 5/2007 | Michelson | | 7,678,136 B2 | 3/2010 | Doubler et al. |
| 7,211,086 B2 | 5/2007 | Biedermann et al. | | 7,678,139 B2 | 3/2010 | Garamszegi et al. |
| 7,211,087 B2 | 5/2007 | Young | | 7,682,375 B2 | 3/2010 | Ritland |
| 7,214,227 B2 | 5/2007 | Colleran et al. | | 7,682,377 B2 | 3/2010 | Konieczynski et al. |
| 7,223,268 B2 | 5/2007 | Biedermann | | 7,686,833 B1 | 3/2010 | Muhanna et al. |
| 7,229,441 B2 | 6/2007 | Trieu et al. | | 7,686,834 B2 | 3/2010 | Saint Martin |
| 7,264,621 B2 | 9/2007 | Coates et al. | | 7,686,835 B2 | 3/2010 | Warnick |
| 7,270,665 B2 | 9/2007 | Morrison et al. | | 7,691,129 B2 | 4/2010 | Felix |
| 7,282,064 B2 | 10/2007 | Chin | | 7,691,131 B2 | 4/2010 | Graf |
| 7,291,151 B2 | 11/2007 | Alvarez | | 7,691,132 B2 | 4/2010 | Landry et al. |
| 7,291,153 B2 | 11/2007 | Glascott | | 7,695,496 B2 | 4/2010 | Labrom et al. |
| 7,294,128 B2 | 11/2007 | Alleyne et al. | | 7,695,497 B2 | 4/2010 | Cordaro et al. |
| 7,294,129 B2 | 11/2007 | Hawkins et al. | | 7,695,498 B2 | 4/2010 | Ritland |

| Patent/Publication | Date | Name |
|---|---|---|
| 7,695,514 B2 | 4/2010 | Kwak |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,233 B2 | 7/2010 | Farr |
| 7,749,258 B2 | 7/2010 | Biedermann et al. |
| 7,758,618 B2 | 7/2010 | Walder et al. |
| 7,763,057 B2 | 7/2010 | Abdelgany et al. |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,819,902 B2 | 10/2010 | Abdelgany et al. |
| 7,909,830 B2 | 3/2011 | Frigg et al. |
| 8,034,084 B2 * | 10/2011 | Landry et al. ............... 606/265 |
| 8,043,343 B2 * | 10/2011 | Miller et al. ............... 606/279 |
| 8,048,129 B2 * | 11/2011 | Forton et al. ............... 606/246 |
| 8,075,592 B2 * | 12/2011 | Landry et al. ............... 606/246 |
| 8,100,915 B2 * | 1/2012 | Jackson ................. 606/86 A |
| 8,162,948 B2 * | 4/2012 | Jackson ................. 606/86 A |
| 2001/0001119 A1 | 5/2001 | Lombardo |
| 2001/0010000 A1 | 7/2001 | Gertzbein |
| 2001/0023350 A1 | 9/2001 | Choi |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0095153 A1 | 7/2002 | Jones et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208203 A1 | 11/2003 | Lim et al. |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Fruediger |
| 2003/0220643 A1 | 11/2003 | Ferree |
| 2003/0225408 A1 | 12/2003 | Nichols et al. |
| 2003/0236529 A1 | 12/2003 | Shluzas et al. |
| 2004/0002708 A1 | 1/2004 | Ritland |
| 2004/0006342 A1 | 1/2004 | Altarac et al. |
| 2004/0039384 A1 | 2/2004 | Boehm |
| 2004/0049189 A1 | 3/2004 | Le Couudic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172025 A1 | 9/2004 | Drewry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0220567 A1 | 11/2004 | Eisermann |
| 2004/0220671 A1 | 11/2004 | Ralph et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0080415 A1 | 4/2005 | Keyer et al. |
| 2005/0085812 A1 | 4/2005 | Sherman |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biedermann et al. |
| 2005/0171543 A1 | 8/2005 | Timm et al. |
| 2005/0177157 A1 | 8/2005 | Jahng |

| | | | | | | |
|---|---|---|---|---|---|---|
| 2005/0182401 A1 | 8/2005 | Timm et al. | | 2006/0036254 A1 | 2/2006 | Lim |
| 2005/0182410 A1 | 8/2005 | Jackson | | 2006/0036256 A1 | 2/2006 | Carl et al. |
| 2005/0187548 A1 | 8/2005 | Butler et al. | | 2006/0036259 A1 | 2/2006 | Carl et al. |
| 2005/0187555 A1 | 8/2005 | Biedermann et al. | | 2006/0036260 A1 | 2/2006 | Runco et al. |
| 2005/0192571 A1 | 9/2005 | Abdelgany | | 2006/0036323 A1 | 2/2006 | Carl et al. |
| 2005/0192580 A1 | 9/2005 | Dalton | | 2006/0036324 A1 | 2/2006 | Sachs et al. |
| 2005/0192589 A1 | 9/2005 | Raymond | | 2006/0041259 A1 | 2/2006 | Paul et al. |
| 2005/0203511 A1 | 9/2005 | Wilson-MacDonald et al. | | 2006/0052780 A1 | 3/2006 | Errico et al. |
| 2005/0203513 A1 | 9/2005 | Jahng et al. | | 2006/0052783 A1 | 3/2006 | Dant et al. |
| 2005/0203514 A1 | 9/2005 | Jahng et al. | | 2006/0052784 A1 | 3/2006 | Dant et al. |
| 2005/0203516 A1 | 9/2005 | Biedermann et al. | | 2006/0052786 A1 | 3/2006 | Dant et al. |
| 2005/0203517 A1 | 9/2005 | Jahng et al. | | 2006/0058788 A1 | 3/2006 | Hammer et al. |
| 2005/0203518 A1 | 9/2005 | Biedermann et al. | | 2006/0058790 A1 | 3/2006 | Carl et al. |
| 2005/0203519 A1 | 9/2005 | Harms et al. | | 2006/0064090 A1 | 3/2006 | Park |
| 2005/0216001 A1 | 9/2005 | David | | 2006/0064091 A1 | 3/2006 | Ludwig et al. |
| 2005/0216003 A1 | 9/2005 | Biedermann et al. | | 2006/0064092 A1 | 3/2006 | Howland |
| 2005/0228400 A1 | 10/2005 | Chao et al. | | 2006/0069390 A1 | 3/2006 | Frigg |
| 2005/0228501 A1 | 10/2005 | Miller et al. | | 2006/0074419 A1 | 4/2006 | Taylor et al. |
| 2005/0234450 A1 | 10/2005 | Barker | | 2006/0079894 A1 | 4/2006 | Colleran et al. |
| 2005/0234451 A1 | 10/2005 | Markworth | | 2006/0079895 A1 | 4/2006 | McLeer |
| 2005/0234452 A1 | 10/2005 | Malandain | | 2006/0079896 A1 | 4/2006 | Kwak |
| 2005/0234453 A1 | 10/2005 | Shaolian et al. | | 2006/0079898 A1 | 4/2006 | Ainsworth |
| 2005/0234454 A1 | 10/2005 | Chin | | 2006/0079899 A1 | 4/2006 | Ritland |
| 2005/0234456 A1 | 10/2005 | Malandain | | 2006/0084977 A1 | 4/2006 | Liebermann |
| 2005/0240181 A1 | 10/2005 | Boomer et al. | | 2006/0084981 A1 | 4/2006 | Shluzas |
| 2005/0240183 A1 | 10/2005 | Vaughan | | 2006/0084982 A1 | 4/2006 | Kim |
| 2005/0245930 A1 | 11/2005 | Timm et al. | | 2006/0084983 A1 | 4/2006 | Kim |
| 2005/0251137 A1 | 11/2005 | Ball | | 2006/0084984 A1 | 4/2006 | Kim |
| 2005/0251139 A1 | 11/2005 | Roh | | 2006/0084985 A1 | 4/2006 | Kim |
| 2005/0251140 A1 | 11/2005 | Shaolian et al. | | 2006/0084987 A1 | 4/2006 | Kim |
| 2005/0251141 A1 | 11/2005 | Frigg et al. | | 2006/0084988 A1 | 4/2006 | Kim |
| 2005/0260058 A1 | 11/2005 | Casagne, III | | 2006/0084989 A1 | 4/2006 | Dickinson et al. |
| 2005/0261685 A1 | 11/2005 | Fortin et al. | | 2006/0084991 A1 | 4/2006 | Borgstrom |
| 2005/0261687 A1 | 11/2005 | Garamszegi et al. | | 2006/0084993 A1 | 4/2006 | Landry et al. |
| 2005/0267470 A1 | 12/2005 | McBride | | 2006/0084995 A1 | 4/2006 | Biedermann et al. |
| 2005/0267471 A1 | 12/2005 | Biedermann et al. | | 2006/0085069 A1 | 4/2006 | Kim |
| 2005/0267474 A1 | 12/2005 | Dalton | | 2006/0089643 A1 | 4/2006 | Mujwid |
| 2005/0267477 A1 | 12/2005 | Jackson | | 2006/0089644 A1 | 4/2006 | Felix |
| 2005/0273099 A1 | 12/2005 | Baccelli et al. | | 2006/0095037 A1 | 5/2006 | Jones et al. |
| 2005/0273101 A1 | 12/2005 | Schumacher | | 2006/0106380 A1 | 5/2006 | Colleran et al. |
| 2005/0277919 A1 | 12/2005 | Slivka et al. | | 2006/0106381 A1 | 5/2006 | Ferree |
| 2005/0277922 A1 | 12/2005 | Trieu et al. | | 2006/0106383 A1 | 5/2006 | Biedermann et al. |
| 2005/0277923 A1 | 12/2005 | Sweeney | | 2006/0111714 A1 | 5/2006 | Foley |
| 2005/0277925 A1 | 12/2005 | Mujwid | | 2006/0111715 A1 | 5/2006 | Jackson |
| 2005/0277927 A1 | 12/2005 | Guenther et al. | | 2006/0116677 A1 | 6/2006 | Burd et al. |
| 2005/0277928 A1 | 12/2005 | Boschert | | 2006/0122597 A1 | 6/2006 | Jojnes et al. |
| 2005/0277931 A1 | 12/2005 | Sweeney et al. | | 2006/0122599 A1 | 6/2006 | Drewry |
| 2005/0277934 A1 | 12/2005 | Vardiman | | 2006/0129147 A1 | 6/2006 | Biedermann et al. |
| 2005/0283152 A1 | 12/2005 | Lindemann et al. | | 2006/0129149 A1 | 6/2006 | Iott et al. |
| 2005/0283157 A1 | 12/2005 | Coates et al. | | 2006/0129239 A1 | 6/2006 | Kwak |
| 2005/0283238 A1 | 12/2005 | Reiley | | 2006/0142758 A1 | 6/2006 | Petit |
| 2005/0283244 A1 | 12/2005 | Gordon et al. | | 2006/0142760 A1 | 6/2006 | McDonnell |
| 2005/0288669 A1 | 12/2005 | Abdou | | 2006/0142761 A1 | 6/2006 | Landry et al. |
| 2005/0288670 A1 | 12/2005 | Panjabi et al. | | 2006/0149228 A1 | 7/2006 | Schlapfer |
| 2005/0288671 A1 | 12/2005 | Yuan et al. | | 2006/0149229 A1 | 7/2006 | Kwak |
| 2005/0288672 A1 | 12/2005 | Ferree | | 2006/0149232 A1 | 7/2006 | Sasing |
| 2005/0288673 A1 | 12/2005 | Catbagan et al. | | 2006/0149238 A1 | 7/2006 | Sherman et al. |
| 2006/0004357 A1 | 1/2006 | Lee et al. | | 2006/0149241 A1 | 7/2006 | Richelsoph et al. |
| 2006/0004359 A1 | 1/2006 | Kramer et al. | | 2006/0149244 A1 | 7/2006 | Amrein et al. |
| 2006/0004360 A1 | 1/2006 | Kramer et al. | | 2006/0155277 A1 | 7/2006 | Metz-Stavenhagen |
| 2006/0004363 A1 | 1/2006 | Brockmeyer et al. | | 2006/0155278 A1 | 7/2006 | Warnick |
| 2006/0009767 A1 | 1/2006 | Kiester | | 2006/0161152 A1 | 7/2006 | Ensign et al. |
| 2006/0009768 A1 | 1/2006 | Ritland | | 2006/0167454 A1 | 7/2006 | Ludwig et al. |
| 2006/0009769 A1 | 1/2006 | Lieberman | | 2006/0167455 A1 | 7/2006 | Clement et al. |
| 2006/0009770 A1 | 1/2006 | Speirs et al. | | 2006/0173454 A1 | 8/2006 | Spitler et al. |
| 2006/0009775 A1 | 1/2006 | Dec et al. | | 2006/0173456 A1 | 8/2006 | Hawkes et al. |
| 2006/0009780 A1 | 1/2006 | Foley et al. | | 2006/0184171 A1 | 8/2006 | Biedermann |
| 2006/0009846 A1 | 1/2006 | Trieu et al. | | 2006/0184180 A1 | 8/2006 | Augostino |
| 2006/0015099 A1 | 1/2006 | Cannon et al. | | 2006/0189983 A1 | 8/2006 | Fallin |
| 2006/0015104 A1 | 1/2006 | Dalton | | 2006/0189984 A1 | 8/2006 | Fallin |
| 2006/0025767 A1 | 2/2006 | Khalili | | 2006/0189985 A1 | 8/2006 | Lewis |
| 2006/0025768 A1 | 2/2006 | Iott et al. | | 2006/0195090 A1 | 8/2006 | Suddaby |
| 2006/0025770 A1 | 2/2006 | Schlapfer et al. | | 2006/0195093 A1 | 8/2006 | Jahng |
| 2006/0030850 A1 | 2/2006 | Keegan et al. | | 2006/0195098 A1 | 8/2006 | Schumacher |
| 2006/0036240 A1 | 2/2006 | Colleran | | 2006/0200128 A1 | 9/2006 | Mueller |
| 2006/0036242 A1 | 2/2006 | Nilsson et al. | | 2006/0200130 A1 | 9/2006 | Hawkins |
| 2006/0036244 A1 | 2/2006 | Spitler et al. | | 2006/0200131 A1 | 9/2006 | Chao et al. |
| 2006/0036246 A1 | 2/2006 | Carl et al. | | 2006/0200132 A1 | 9/2006 | Chao et al. |
| 2006/0036252 A1 | 2/2006 | Baynham et al. | | 2006/0200135 A1 | 9/2006 | Sherman et al. |

| | | | | | |
|---|---|---|---|---|---|
| 2006/0200138 A1 | 9/2006 | Michelson | 2007/0055238 A1 | 3/2007 | Biedermann et al. |
| 2006/0200139 A1 | 9/2006 | Michelson | 2007/0055239 A1 | 3/2007 | Sweeney et al. |
| 2006/0200149 A1 | 9/2006 | Hoy et al. | 2007/0055240 A1 | 3/2007 | Matthis et al. |
| 2006/0210494 A1 | 9/2006 | Rabiei et al. | 2007/0055241 A1 | 3/2007 | Matthis et al. |
| 2006/0212033 A1 | 9/2006 | Rothman | 2007/0055242 A1 | 3/2007 | Bailly |
| 2006/0212034 A1 | 9/2006 | Triplett et al. | 2007/0055244 A1 | 3/2007 | Jackson |
| 2006/0217713 A1 | 9/2006 | Serhan et al. | 2007/0055247 A1 | 3/2007 | Jahng |
| 2006/0217714 A1 | 9/2006 | Serhan et al. | 2007/0073289 A1 | 3/2007 | Kwak |
| 2006/0217716 A1 | 9/2006 | Baker et al. | 2007/0073290 A1 | 3/2007 | Boehm, Jr. |
| 2006/0217719 A1 | 9/2006 | Albert et al. | 2007/0073291 A1 | 3/2007 | Cordaro et al. |
| 2006/0229608 A1 | 10/2006 | Foster | 2007/0073293 A1 | 3/2007 | Martz |
| 2006/0229609 A1 | 10/2006 | Wang | 2007/0073405 A1 | 3/2007 | Verhulst et al. |
| 2006/0229612 A1 | 10/2006 | Rothman | 2007/0078460 A1 | 4/2007 | Frigg et al. |
| 2006/0229613 A1 | 10/2006 | Timm | 2007/0078461 A1 | 4/2007 | Shluzas |
| 2006/0229614 A1 | 10/2006 | Foley et al. | 2007/0083199 A1 | 4/2007 | Baccelli |
| 2006/0229615 A1 | 10/2006 | Abdou | 2007/0088357 A1 | 4/2007 | Johnson et al. |
| 2006/0235389 A1 | 10/2006 | Albert et al. | 2007/0088359 A1 | 4/2007 | Woods et al. |
| 2006/0235392 A1 | 10/2006 | Hammer et al. | 2007/0093813 A1 | 4/2007 | Callahan, II et al. |
| 2006/0235393 A1 | 10/2006 | Bono et al. | 2007/0093814 A1 | 4/2007 | Callahan, II et al. |
| 2006/0241593 A1 | 10/2006 | Sherman et al. | 2007/0093815 A1 | 4/2007 | Callahan, II et al. |
| 2006/0241595 A1 | 10/2006 | Molz, IV et al. | 2007/0093817 A1 | 4/2007 | Barrus et al. |
| 2006/0241599 A1 | 10/2006 | Konieczynski et al. | 2007/0093818 A1 | 4/2007 | Biedermann et al. |
| 2006/0241600 A1 | 10/2006 | Ensign et al. | 2007/0093819 A1 | 4/2007 | Albert |
| 2006/0241769 A1 | 10/2006 | Gordon | 2007/0093824 A1 | 4/2007 | Hestad et al. |
| 2006/0241771 A1 | 10/2006 | Gordon | 2007/0093826 A1 | 4/2007 | Hawkes et al. |
| 2006/0247624 A1 | 11/2006 | Banouskou et al. | 2007/0093827 A1 | 4/2007 | Warnick |
| 2006/0247630 A1 | 11/2006 | Iott et al. | 2007/0093828 A1 | 4/2007 | Abdou |
| 2006/0247631 A1 | 11/2006 | Ahn et al. | 2007/0093831 A1 | 4/2007 | Abdelgany et al. |
| 2006/0247632 A1 | 11/2006 | Winslow | 2007/0093833 A1 | 4/2007 | Kuiper et al. |
| 2006/0247633 A1 | 11/2006 | Winslow | 2007/0100341 A1 | 5/2007 | Reglos et al. |
| 2006/0247635 A1 | 11/2006 | Gordon | 2007/0118117 A1 | 5/2007 | Altarac et al. |
| 2006/0247636 A1 | 11/2006 | Yuan et al. | 2007/0118118 A1 | 5/2007 | Kwak et al. |
| 2006/0247637 A1 | 11/2006 | Colleran | 2007/0118119 A1 | 5/2007 | Hestad |
| 2006/0247779 A1 | 11/2006 | Gordon | 2007/0118122 A1 | 5/2007 | Butler et al. |
| 2006/0264933 A1 | 11/2006 | Baker et al. | 2007/0118123 A1 | 5/2007 | Strausbaugh et al. |
| 2006/0264934 A1 | 11/2006 | Fallin | 2007/0118124 A1 | 5/2007 | Biedermann et al. |
| 2006/0264935 A1 | 11/2006 | White | 2007/0123862 A1 | 5/2007 | Warnick |
| 2006/0264936 A1 | 11/2006 | Partin et al. | 2007/0123864 A1 | 5/2007 | Walder et al. |
| 2006/0264937 A1 | 11/2006 | White | 2007/0123865 A1 | 5/2007 | Schlapfer et al. |
| 2006/0264940 A1 | 11/2006 | Hartmannt | 2007/0123866 A1 | 5/2007 | Gerbec et al. |
| 2006/0264942 A1 | 11/2006 | Lim et al. | 2007/0123867 A1 | 5/2007 | Kirschman |
| 2006/0264962 A1 | 11/2006 | Chin et al. | 2007/0123870 A1 | 5/2007 | Jeon et al. |
| 2006/0276787 A1 | 12/2006 | Zubok et al. | 2007/0123871 A1 | 5/2007 | Jahng |
| 2006/0276789 A1 | 12/2006 | Jackson | 2007/0129729 A1 | 6/2007 | Petit et al. |
| 2006/0276791 A1 | 12/2006 | Shluzas | 2007/0135815 A1 | 6/2007 | Gerbec et al. |
| 2006/0276792 A1 | 12/2006 | Ensign et al. | 2007/0161986 A1 | 7/2007 | Levy |
| 2006/0282074 A1 | 12/2006 | Renaud et al. | 2007/0161991 A1 | 7/2007 | Altarac et al. |
| 2006/0282075 A1 | 12/2006 | Labrom | 2007/0161994 A1 | 7/2007 | Lowery et al. |
| 2006/0282076 A1 | 12/2006 | Labrom | 2007/0161995 A1 | 7/2007 | Trautwein et al. |
| 2006/0282077 A1 | 12/2006 | Labrom | 2007/0161996 A1 | 7/2007 | Biedermann et al. |
| 2006/0282078 A1 | 12/2006 | Labrom | 2007/0161997 A1 | 7/2007 | Thramann et al. |
| 2006/0282079 A1 | 12/2006 | Labrom | 2007/0161999 A1 | 7/2007 | Biedermann et al. |
| 2006/0282080 A1 | 12/2006 | Albert | 2007/0167948 A1 | 7/2007 | Abdou |
| 2006/0293657 A1 | 12/2006 | Hartmann | 2007/0167949 A1 | 7/2007 | Altarac et al. |
| 2006/0293659 A1 | 12/2006 | Alvarez | 2007/0173818 A1 | 7/2007 | Hestad et al. |
| 2006/0293663 A1 | 12/2006 | Walkenhorst | 2007/0173819 A1 | 7/2007 | Sandlin |
| 2006/0293665 A1 | 12/2006 | Shluzas | 2007/0173820 A1 | 7/2007 | Trieu |
| 2006/0293666 A1 | 12/2006 | Matthis et al. | 2007/0173822 A1 | 7/2007 | Bruneau et al. |
| 2007/0005062 A1 | 1/2007 | Lange | 2007/0173828 A1 | 7/2007 | Firkins et al. |
| 2007/0005063 A1 | 1/2007 | Bruneau | 2007/0173832 A1 | 7/2007 | Tebbe et al. |
| 2007/0005137 A1 | 1/2007 | Kwak | 2007/0191839 A1 | 8/2007 | Justis et al. |
| 2007/0016188 A1 | 1/2007 | Boehm, Jr. et al. | 2007/0191841 A1 | 8/2007 | Justis et al. |
| 2007/0016190 A1 | 1/2007 | Martinez | 2007/0191846 A1 | 8/2007 | Bruneau et al. |
| 2007/0016193 A1 | 1/2007 | Ritland | 2007/0198014 A1 | 8/2007 | Graf et al. |
| 2007/0016194 A1 | 1/2007 | Shaolian et al. | 2007/0208344 A1 | 9/2007 | Young |
| 2007/0016198 A1 | 1/2007 | Boehm, Jr. et al. | 2007/0213720 A1 | 9/2007 | Gordon et al. |
| 2007/0016199 A1 | 1/2007 | Boehm, Jr. et al. | 2007/0225707 A1 | 9/2007 | Wisnewski et al. |
| 2007/0021750 A1 | 1/2007 | Shluzas et al. | 2007/0225708 A1 | 9/2007 | Biedermann et al. |
| 2007/0043355 A1 | 2/2007 | Bette et al. | 2007/0225710 A1 | 9/2007 | Jahng et al. |
| 2007/0043356 A1 | 2/2007 | Timm | 2007/0225711 A1 | 9/2007 | Ensign |
| 2007/0043357 A1 | 2/2007 | Kirschman | 2007/0233064 A1 | 10/2007 | Holt |
| 2007/0043358 A1 | 2/2007 | Molz, IV et al. | 2007/0233073 A1 | 10/2007 | Wisnewski et al. |
| 2007/0043359 A1 | 2/2007 | Altarac et al. | 2007/0233075 A1 | 10/2007 | Dawson |
| 2007/0043364 A1 | 2/2007 | Cawley et al. | 2007/0233078 A1 | 10/2007 | Justis et al. |
| 2007/0049931 A1 | 3/2007 | Justis et al. | 2007/0233080 A1 | 10/2007 | Na et al. |
| 2007/0049933 A1 | 3/2007 | Ahn et al. | 2007/0233085 A1 | 10/2007 | Biedermann et al. |
| 2007/0049936 A1 | 3/2007 | Colleran | 2007/0233086 A1 | 10/2007 | Harms et al. |
| 2007/0055235 A1 | 3/2007 | Janowski et al. | 2007/0233087 A1 | 10/2007 | Schlapfer |
| 2007/0055236 A1 | 3/2007 | Hudgins | 2007/0233092 A1 | 10/2007 | Falahee |

| | | | | | |
|---|---|---|---|---|---|
| 2007/0233094 A1 | 10/2007 | Colleran et al. | 2008/0161859 A1 | 7/2008 | Nilsson |
| 2007/0233095 A1 | 10/2007 | Schlaepfer | 2008/0161863 A1 | 7/2008 | Arnold et al. |
| 2007/0250061 A1 | 10/2007 | Chin et al. | 2008/0167687 A1 | 7/2008 | Colleran et al. |
| 2007/0260246 A1 | 11/2007 | Biedermann | 2008/0177316 A1 | 7/2008 | Bergeronk et al. |
| 2007/0270806 A1 | 11/2007 | Foley et al. | 2008/0177317 A1 | 7/2008 | Jackson |
| 2007/0270807 A1 | 11/2007 | Armstrong et al. | 2008/0177319 A1 | 7/2008 | Schwab |
| 2007/0270810 A1 | 11/2007 | Sanders | 2008/0177321 A1 | 7/2008 | Drewry et al. |
| 2007/0270813 A1 | 11/2007 | Garamszegi | 2008/0177322 A1 | 7/2008 | Davis et al. |
| 2007/0270814 A1 | 11/2007 | Lim et al. | 2008/0177327 A1 | 7/2008 | Malandain et al. |
| 2007/0270815 A1 | 11/2007 | Johnson et al. | 2008/0177332 A1 | 7/2008 | Reiley et al. |
| 2007/0270821 A1 | 11/2007 | Trieu et al. | 2008/0183212 A1 | 7/2008 | Veldman et al. |
| 2007/0270830 A1 | 11/2007 | Morrison | 2008/0183213 A1 | 7/2008 | Veldman et al. |
| 2007/0270831 A1 | 11/2007 | Dewey et al. | 2008/0183215 A1 | 7/2008 | Altarac et al. |
| 2007/0270832 A1 | 11/2007 | Moore | 2008/0183216 A1 | 7/2008 | Jackson |
| 2007/0270835 A1 | 11/2007 | Wisnewski | 2008/0183219 A1 | 7/2008 | Bertram |
| 2007/0270837 A1 | 11/2007 | Eckhardt et al. | 2008/0183223 A1 | 7/2008 | Jeon et al. |
| 2007/0270838 A1 | 11/2007 | Bruneau et al. | 2008/0195100 A1 | 8/2008 | Capote et al. |
| 2007/0270839 A1 | 11/2007 | Jeon et al. | 2008/0195153 A1 | 8/2008 | Thompson |
| 2007/0270843 A1 | 11/2007 | Matthis et al. | 2008/0195159 A1 | 8/2008 | Kloss et al. |
| 2007/0276380 A1 | 11/2007 | Jahng et al. | 2008/0200956 A1 | 8/2008 | Beckwith et al. |
| 2007/0288004 A1 | 12/2007 | Alvarez | 2008/0215095 A1 | 9/2008 | Biedermann et al. |
| 2007/0288008 A1 | 12/2007 | Park | 2008/0221620 A1 | 9/2008 | Krause |
| 2007/0288009 A1 | 12/2007 | Brown et al. | 2008/0221692 A1 | 9/2008 | Zucherman et al. |
| 2007/0288011 A1 | 12/2007 | Logan | 2008/0228227 A1 | 9/2008 | Brown et al. |
| 2007/0288012 A1 | 12/2007 | Colleran et al. | 2008/0228229 A1 | 9/2008 | Walder et al. |
| 2008/0009862 A1 | 1/2008 | Hoffman | 2008/0234691 A1 | 9/2008 | Schwab |
| 2008/0009864 A1 | 1/2008 | Forton et al. | 2008/0234734 A1 | 9/2008 | Walder et al. |
| 2008/0015578 A1 | 1/2008 | Erickson et al. | 2008/0234736 A1 | 9/2008 | Trieu et al. |
| 2008/0015579 A1 | 1/2008 | Whipple | 2008/0234737 A1 | 9/2008 | Bosehert |
| 2008/0015580 A1 | 1/2008 | Chao | 2008/0234739 A1 | 9/2008 | Hudgins et al. |
| 2008/0015584 A1 | 1/2008 | Richelsoph | 2008/0234744 A1 | 9/2008 | Zylber et al. |
| 2008/0015586 A1 | 1/2008 | Krishna et al. | 2008/0234746 A1 | 9/2008 | Jahng et al. |
| 2008/0021454 A1 | 1/2008 | Chao et al. | 2008/0234756 A1 | 9/2008 | Sutcliffe et al. |
| 2008/0021455 A1 | 1/2008 | Chao et al. | 2008/0234759 A1 | 9/2008 | Marino |
| 2008/0021458 A1 | 1/2008 | Lim | 2008/0243188 A1 | 10/2008 | Walder et al. |
| 2008/0021459 A1 | 1/2008 | Lim | 2008/0249570 A1 | 10/2008 | Carson et al. |
| 2008/0021462 A1 | 1/2008 | Trieu | 2008/0249576 A1 | 10/2008 | Wawkes et al. |
| 2008/0021464 A1 | 1/2008 | Norin et al. | 2008/0255617 A1 | 10/2008 | Cho et al. |
| 2008/0021465 A1 | 1/2008 | Shadduck et al. | 2008/0262546 A1 | 10/2008 | Calvosa et al. |
| 2008/0021466 A1 | 1/2008 | Shadduck et al. | 2008/0262548 A1 | 10/2008 | Lange et al. |
| 2008/0021473 A1 | 1/2008 | Butler et al. | 2008/0262552 A1 | 10/2008 | Kim |
| 2008/0027432 A1 | 1/2008 | Strauss et al. | 2008/0262554 A1 | 10/2008 | Hayes et al. |
| 2008/0033435 A1 | 2/2008 | Studer et al. | 2008/0262556 A1 | 10/2008 | Jacofsky et al. |
| 2008/0039838 A1 | 2/2008 | Landry et al. | 2008/0269742 A1 | 10/2008 | Levy et al. |
| 2008/0039843 A1 | 2/2008 | Abdou | 2008/0269804 A1 | 10/2008 | Holt |
| 2008/0045951 A1 | 2/2008 | Fanger et al. | 2008/0269809 A1 | 10/2008 | Garamszegi |
| 2008/0045955 A1 | 2/2008 | Berrevoets et al. | 2008/0275504 A1 | 11/2008 | Bonin et al. |
| 2008/0045957 A1 | 2/2008 | Landry et al. | 2008/0287994 A1 | 11/2008 | Perez-Cruet et al. |
| 2008/0051780 A1 | 2/2008 | Vaidya et al. | 2008/0288002 A1 | 11/2008 | Crall et al. |
| 2008/0051787 A1 | 2/2008 | Remington et al. | 2008/0300630 A1 | 12/2008 | Bohnema et al. |
| 2008/0058811 A1 | 3/2008 | Alleyne et al. | 2008/0300633 A1 | 12/2008 | Jackson |
| 2008/0058812 A1 | 3/2008 | Zehnder | 2008/0306528 A1 | 12/2008 | Winslow et al. |
| 2008/0065071 A1 | 3/2008 | Park | 2008/0306533 A1 | 12/2008 | Winslow et al. |
| 2008/0065073 A1 | 3/2008 | Perriello et al. | 2008/0306536 A1 | 12/2008 | Frig et al. |
| 2008/0065075 A1 | 3/2008 | Dant | 2008/0306539 A1 | 12/2008 | Cain et al. |
| 2008/0065077 A1 | 3/2008 | Ferree | 2008/0306540 A1 | 12/2008 | Mitchell et al. |
| 2008/0065079 A1 | 3/2008 | Bruneau et al. | 2008/0306543 A1 | 12/2008 | Cain et al. |
| 2008/0071273 A1 | 3/2008 | Hawkes et al. | 2008/0306545 A1 | 12/2008 | Winslow |
| 2008/0071274 A1 | 3/2008 | Ensign | 2008/0312655 A1 | 12/2008 | Kirschman et al. |
| 2008/0071277 A1 | 3/2008 | Warnick | 2008/0312692 A1 | 12/2008 | Brennan et al. |
| 2008/0077139 A1 | 3/2008 | Landry et al. | 2008/0312694 A1 | 12/2008 | Peterman et al. |
| 2008/0086131 A1 | 4/2008 | Daly et al. | 2008/0312696 A1 | 12/2008 | Butters et al. |
| 2008/0086132 A1 | 4/2008 | Biedermann et al. | 2008/0312701 A1 | 12/2008 | Butters et al. |
| 2008/0091214 A1 | 4/2008 | Richelsoph | 2009/0005787 A1 | 1/2009 | Crall et al. |
| 2008/0097431 A1 | 4/2008 | Vessa | 2009/0005813 A1 | 1/2009 | Crall et al. |
| 2008/0097434 A1 | 4/2008 | Moumene et al. | 2009/0005814 A1 | 1/2009 | Miller et al. |
| 2008/0097441 A1 | 4/2008 | Hayes et al. | 2009/0005817 A1 | 1/2009 | Friedrich et al. |
| 2008/0097457 A1 | 4/2008 | Warnick | 2009/0012567 A1 | 1/2009 | Biedermann et al. |
| 2008/0108992 A1 | 5/2008 | Barry et al. | 2009/0018583 A1 | 1/2009 | Song et al. |
| 2008/0119858 A1 | 5/2008 | Potash | 2009/0018591 A1 | 1/2009 | Hawkes et al. |
| 2008/0125777 A1 | 5/2008 | Veldman et al. | 2009/0024165 A1 | 1/2009 | Ferree |
| 2008/0125787 A1 | 5/2008 | Doubler et al. | 2009/0024169 A1 | 1/2009 | Triplett et al. |
| 2008/0132952 A1 | 6/2008 | Malandain et al. | 2009/0030457 A1 | 1/2009 | Janowski et al. |
| 2008/0140075 A1 | 6/2008 | Ensign et al. | 2009/0030464 A1 | 1/2009 | Hestad et al. |
| 2008/0140076 A1 | 6/2008 | Jackson | 2009/0030465 A1 | 1/2009 | Altarac et al. |
| 2008/0140133 A1 | 6/2008 | Allard et al. | 2009/0036929 A1 | 2/2009 | Reglos et al. |
| 2008/0147122 A1 | 6/2008 | Jackson | 2009/0036932 A1 | 2/2009 | Rouyer et al. |
| 2008/0154307 A1 | 6/2008 | Colleran et al. | 2009/0036934 A1 | 2/2009 | Biedermann et al. |
| 2008/0161854 A1 | 7/2008 | Bae et al. | 2009/0048631 A1 | 2/2009 | Bhatnagar et al. |

| | | | | | | |
|---|---|---|---|---|---|---|
| 2009/0054932 A1 | 2/2009 | Butler et al. | | 2009/0270921 A1 | 10/2009 | Krause |
| 2009/0062860 A1 | 3/2009 | Frasier et al. | | 2009/0270922 A1 | 10/2009 | Biedermann et al. |
| 2009/0062865 A1 | 3/2009 | Schumacher | | 2009/0275981 A1 | 11/2009 | Abdelgany et al. |
| 2009/0062867 A1 | 3/2009 | Schumacher | | 2009/0275983 A1 | 11/2009 | Veldman et al. |
| 2009/0062914 A1 | 3/2009 | Marino | | 2009/0275986 A1 | 11/2009 | Prevost et al. |
| 2009/0069849 A1 | 3/2009 | Oh et al. | | 2009/0281571 A1 | 11/2009 | Weaver et al. |
| 2009/0069852 A1 | 3/2009 | Farris et al. | | 2009/0281572 A1 | 11/2009 | White |
| 2009/0069853 A1 | 3/2009 | Schumacher | | 2009/0281573 A1 | 11/2009 | Biedermann et al. |
| 2009/0076550 A1 | 3/2009 | Bernhardt, Jr. et al. | | 2009/0287250 A1 | 11/2009 | Molz, IV et al. |
| 2009/0076552 A1 | 3/2009 | Tornier | | 2009/0287251 A1 | 11/2009 | Bae et al. |
| 2009/0082809 A1 | 3/2009 | Nguyen et al. | | 2009/0287252 A1 | 11/2009 | Marik et al. |
| 2009/0082812 A1 | 3/2009 | Lewis | | 2009/0287253 A1 | 11/2009 | Felix et al. |
| 2009/0082815 A1 | 3/2009 | Zylber et al. | | 2009/0299411 A1 | 12/2009 | Laskowitz et al. |
| 2009/0082819 A1 | 3/2009 | Blain et al. | | 2009/0299415 A1 | 12/2009 | Pimenta |
| 2009/0088782 A1 | 4/2009 | Moumene et al. | | 2009/0306719 A1 | 12/2009 | Meyer, III et al. |
| 2009/0088799 A1 | 4/2009 | Yeh | | 2009/0306720 A1 | 12/2009 | Doubler et al. |
| 2009/0088803 A1 | 4/2009 | Justis et al. | | 2009/0312804 A1 | 12/2009 | Gamache et al. |
| 2009/0088807 A1 | 4/2009 | Castaneda et al. | | 2009/0318968 A1 | 12/2009 | Duggal et al. |
| 2009/0093820 A1 | 4/2009 | Trieu et al. | | 2009/0326582 A1 | 12/2009 | Songer et al. |
| 2009/0093843 A1 | 4/2009 | Lemoine et al. | | 2009/0326583 A1 | 12/2009 | Moumene et al. |
| 2009/0093845 A1 | 4/2009 | Hestad et al. | | 2009/0326587 A1 | 12/2009 | Matthis et al. |
| 2009/0093846 A1 | 4/2009 | Hestad et al. | | 2010/0004692 A1 | 1/2010 | Biedermann et al. |
| 2009/0099606 A1 | 4/2009 | Hestad et al. | | 2010/0010540 A1 | 1/2010 | Park |
| 2009/0099607 A1 | 4/2009 | Fallin et al. | | 2010/0010544 A1 | 1/2010 | Fallin et al. |
| 2009/0099608 A1 | 4/2009 | Szczesny | | 2010/0016898 A1 | 1/2010 | Shluzas |
| 2009/0105760 A1 | 4/2009 | Frey | | 2010/0030271 A1 | 2/2010 | Winslow et al. |
| 2009/0105769 A1 | 4/2009 | Rock et al. | | 2010/0036420 A1 | 2/2010 | Kalfas et al. |
| 2009/0105770 A1 | 4/2009 | Berrevoets et al. | | 2010/0036422 A1 | 2/2010 | Flynn et al. |
| 2009/0105771 A1 | 4/2009 | Lei et al. | | 2010/0036423 A1 | 2/2010 | Hayes et al. |
| 2009/0112265 A1 | 4/2009 | Hudgins et al. | | 2010/0036424 A1 | 2/2010 | Fielding et al. |
| 2009/0112266 A1 | 4/2009 | Weng et al. | | 2010/0036425 A1 | 2/2010 | Barrus et al. |
| 2009/0112267 A1 | 4/2009 | Atkinson et al. | | 2010/0042155 A1 | 2/2010 | Biedermann et al. |
| 2009/0118767 A1 | 5/2009 | Hestad et al. | | 2010/0042156 A1 | 2/2010 | Harms et al. |
| 2009/0118772 A1 | 5/2009 | Diederich et al. | | 2010/0049254 A1 | 2/2010 | Biedermann et al. |
| 2009/0125063 A1 | 5/2009 | Panjabi | | 2010/0057125 A1 | 3/2010 | Viker |
| 2009/0131981 A1 | 5/2009 | White | | 2010/0057126 A1 | 3/2010 | Hestad |
| 2009/0131983 A1 | 5/2009 | Biedermann | | 2010/0063544 A1 | 3/2010 | Butler |
| 2009/0138044 A1 | 5/2009 | Bergeron et al. | | 2010/0063545 A1 | 3/2010 | Richelsoph |
| 2009/0138052 A1 | 5/2009 | Biedermann et al. | | 2010/0063547 A1 | 3/2010 | Morin et al. |
| 2009/0143827 A1 | 6/2009 | Levy et al. | | 2010/0063550 A1 | 3/2010 | Felix et al. |
| 2009/0143829 A1 | 6/2009 | Shluzas | | 2010/0063551 A1 | 3/2010 | Richelsoph |
| 2009/0149885 A1 | 6/2009 | Durward et al. | | 2010/0063553 A1 | 3/2010 | Warnick |
| 2009/0149887 A1 | 6/2009 | Schlaepfer et al. | | 2010/0069963 A1 | 3/2010 | Eckman |
| 2009/0163953 A1 | 6/2009 | Biedermann et al. | | 2010/0069964 A1 | 3/2010 | Lechmann |
| 2009/0163954 A1 | 6/2009 | Kwak | | 2010/0069969 A1 | 3/2010 | Ampuero et al. |
| 2009/0163955 A1 | 6/2009 | Moumene et al. | | 2010/0087858 A1 | 4/2010 | Abdou |
| 2009/0163956 A1 | 6/2009 | Biedermann et al. | | 2010/0087861 A1 | 4/2010 | Lechmann et al. |
| 2009/0163961 A1 | 6/2009 | Kirschman | | 2010/0087862 A1 | 4/2010 | Biedermann et al. |
| 2009/0163963 A1 | 6/2009 | Berrevoets | | 2010/0087863 A1 | 4/2010 | Biedermann et al. |
| 2009/0171395 A1 | 7/2009 | Jeon et al. | | 2010/0087865 A1 | 4/2010 | Biedermann et al. |
| 2009/0177232 A1 | 7/2009 | Kiester | | 2010/0094343 A1 | 4/2010 | Pham et al. |
| 2009/0182380 A1 | 7/2009 | Abdelgany | | 2010/0094345 A1 | 4/2010 | Saidha et al. |
| 2009/0192548 A1 | 7/2009 | Jeon et al. | | 2010/0094348 A1 | 4/2010 | Biedermann et al. |
| 2009/0192551 A1 | 7/2009 | Cianfrani et al. | | 2010/0094349 A1 | 4/2010 | Hammer et al. |
| 2009/0198280 A1 | 8/2009 | Spratt et al. | | 2010/0094352 A1 | 4/2010 | Iott et al. |
| 2009/0198281 A1 | 8/2009 | Rice et al. | | 2010/0094353 A1 | 4/2010 | Shim et al. |
| 2009/0198289 A1 | 8/2009 | Manderson | | 2010/0100136 A1 | 4/2010 | Won et al. |
| 2009/0198291 A1 | 8/2009 | Kevin et al. | | 2010/0100137 A1 | 4/2010 | Justis et al. |
| 2009/0204155 A1 | 8/2009 | Aschmann | | 2010/0106189 A1 | 4/2010 | Miller |
| 2009/0216280 A1 | 8/2009 | Hutchinson | | 2010/0114170 A1 | 5/2010 | Barrus et al. |
| 2009/0228045 A1 | 9/2009 | Hayes et al. | | 2010/0114171 A1 | 5/2010 | Boachie-Adjei et al. |
| 2009/0240286 A1 | 9/2009 | Friedrich et al. | | 2010/0114180 A1 | 5/2010 | Rock et al. |
| 2009/0240287 A1 | 9/2009 | Cunliffe et al. | | 2010/0125302 A1 | 5/2010 | Hammill, Sr. et al. |
| 2009/0248030 A1 | 10/2009 | Butler et al. | | 2010/0131017 A1 | 5/2010 | Farris et al. |
| 2009/0248075 A1 | 10/2009 | Ogilvie et al. | | 2010/0131018 A1 | 5/2010 | Konieczynski et al. |
| 2009/0248077 A1 | 10/2009 | Johns | | 2010/0137918 A1 | 6/2010 | Wilcox et al. |
| 2009/0248081 A1 | 10/2009 | LeHuec et al. | | 2010/0137920 A1 | 6/2010 | Hammill, Sr. et al. |
| 2009/0248083 A1 | 10/2009 | Patterson et al. | | 2010/0145390 A1 | 6/2010 | McCarthy et al. |
| 2009/0248088 A1 | 10/2009 | Biedermann | | 2010/0152776 A1 | 6/2010 | Keyer et al. |
| 2009/0254123 A1 | 10/2009 | Pafford et al. | | 2010/0152785 A1 | 6/2010 | Forton et al. |
| 2009/0254125 A1 | 10/2009 | Predick | | 2010/0152787 A1 | 6/2010 | Walsh et al. |
| 2009/0259254 A1 | 10/2009 | Pisharodi | | 2010/0152788 A1 | 6/2010 | Warnick |
| 2009/0259257 A1 | 10/2009 | Prevost | | 2010/0160965 A1 | 6/2010 | Viker |
| 2009/0259258 A1 | 10/2009 | Perez-Cruet et al. | | 2010/0160974 A1 | 6/2010 | Viker |
| 2009/0264896 A1 | 10/2009 | Biedermann et al. | | 2010/0160980 A1 | 6/2010 | Walsh et al. |
| 2009/0264933 A1 | 10/2009 | Carls et al. | | 2010/0168796 A1 | 7/2010 | Eliasen et al. |
| 2009/0270916 A1 | 10/2009 | Ramsay et al. | | 2010/0168800 A1 | 7/2010 | Biedermann et al. |
| 2009/0270917 A1 | 10/2009 | Boehm | | 2010/0168801 A1 | 7/2010 | Biedermann et al. |
| 2009/0270920 A1 | 10/2009 | Douget et al. | | 2010/0174322 A1 | 7/2010 | Abdelgany et al. |

| | | | |
|---|---|---|---|
| 2010/0179603 A1 | 7/2010 | Warnick | |
| 2010/0185247 A1 | 7/2010 | Richelsoph | |
| 2010/0191290 A1 | 7/2010 | Felix | |
| 2010/0198269 A1 | 8/2010 | Taylor et al. | |
| 2010/0198270 A1 | 8/2010 | Barker et al. | |
| 2010/0198272 A1 | 8/2010 | Keyer et al. | |
| 2010/0204735 A1 | 8/2010 | Gephart et al. | |
| 2010/0222822 A1 | 9/2010 | Farris et al. | |
| 2010/0228293 A1 | 9/2010 | Courtney et al. | |
| 2010/0234891 A1 | 9/2010 | Freeman et al. | |
| 2010/0241170 A1 | 9/2010 | Cammisa et al. | |
| 2010/0249846 A1 | 9/2010 | Simonson | |
| 2010/0249856 A1 | 9/2010 | Iott et al. | |
| 2010/0256681 A1 | 10/2010 | Hammer et al. | |
| 2010/0256682 A1 | 10/2010 | Fallin et al. | |
| 2010/0262196 A1 | 10/2010 | Barrus et al. | |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1210914 | 6/2002 |
| EP | 1570795 | 2/2005 |
| EP | 1579816 | 9/2005 |
| EP | 1634537 | 3/2006 |
| EP | 1925263 | 5/2008 |
| ES | 2000325358 | 3/2000 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| FR | 2925288 | 6/2009 |
| GB | 1519139 | 7/1978 |
| GB | 2365345 | 2/2002 |
| GB | 2382304 | 5/2003 |
| JP | 10277070 | 10/1998 |
| SU | 313538 | 10/1971 |
| WO | WO92/03100 | 3/1992 |
| WO | WO94/10927 | 5/1994 |
| WO | WO94/26191 | 11/1994 |
| WO | WO96/41582 | 12/1996 |
| WO | WO01/10317 | 2/2001 |
| WO | WO01/28436 | 4/2001 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/013839 | 2/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | WO2006/045094 | 4/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088731 | 7/2008 |
| WO | WO2008/088990 | 7/2008 |
| WO | WO2008/089075 | 7/2008 |
| WO | WO2008/140756 | 11/2008 |
| WO | WO2009/015100 | 1/2009 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

Brochure of Spinal Concepts, an Abbott Laboratories Company, *Pathfinder, Minimally Invasive Pedicle Fixation System*, Publication Date: Nov. 2003.
Brochure of Spinal Concepts, *InCompass, Thoracolumbar Fixation System*, Publication Date: Oct. 2003.
Brochure of Spinal Concepts, Surgical Technique, *InCompass, Thoracolumbar Fixation System*, Publication Date: Oct. 2003.
Brochure of SpineLine, Current Concepts, *Minimally Invasive Posterior Spinal Decompression and Fusion Procedures*, Publication Date: Sep./Oct. 2003.
Brochure of Sofamor Danek the Spine Specialist, TSRH, *Pedicle Screw Spinal System*, Publication Date: Jan. 23, 1995.
Brochure of Tyco/Healthcare/Surgical Dynamics on Spiral Radius 90D, Publication Date: Sep. 2001, pp. 1-8.
Brochure of Zimmer Spine, Inc., Dynesys® LIS Less Invasive Surgery, The Dynamic Stabilization System, Publication Date: 2005.
Claris Instrumentation Brochure, G Med, pub. 1997.
EBI Omega 21 Brochure, EBI Spine Systems, pub. 1999.
SDRS Surgical Dynamics Rod System Brochure, Surgical Dynamics, pub. 1998-99.
The Rod Plate System Brochure, Stryker Howmedica Osteonics, pub. Oct. 1999.
Versalok Low Back Fixation System Brochure, Wright Medical Technology, Inc., pub. 1997.
VLS System Variable Locking Screw Brochure, Interpore Cross International, 1999.

\* cited by examiner

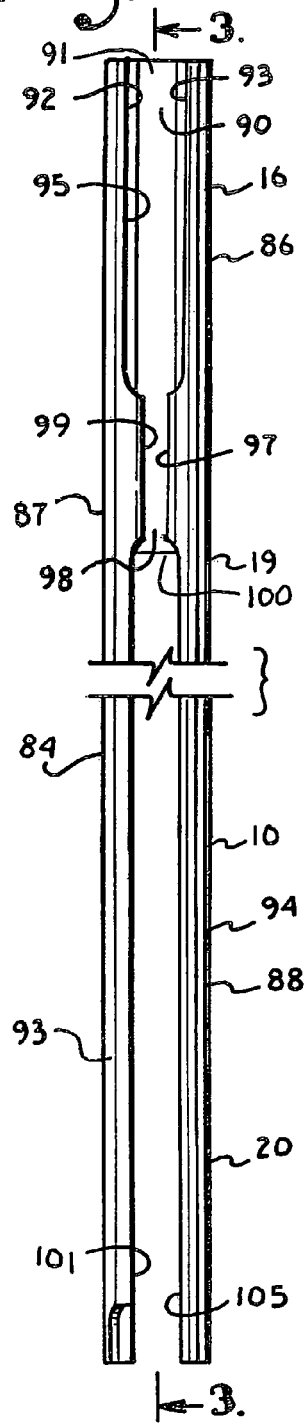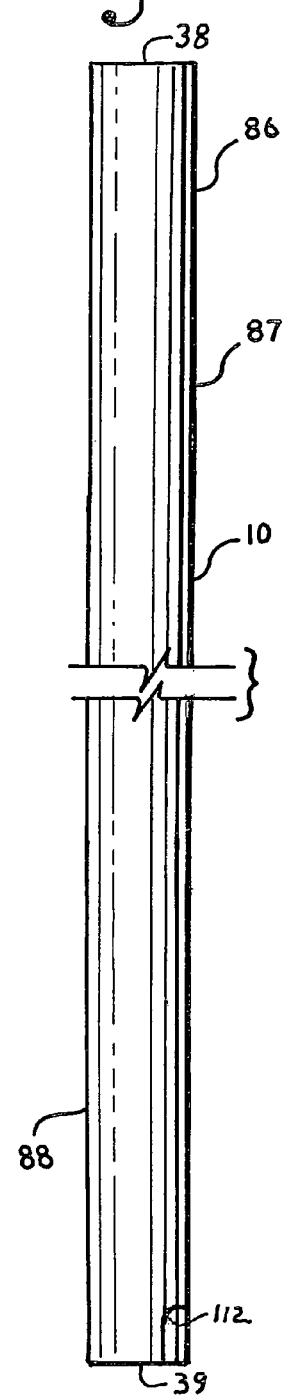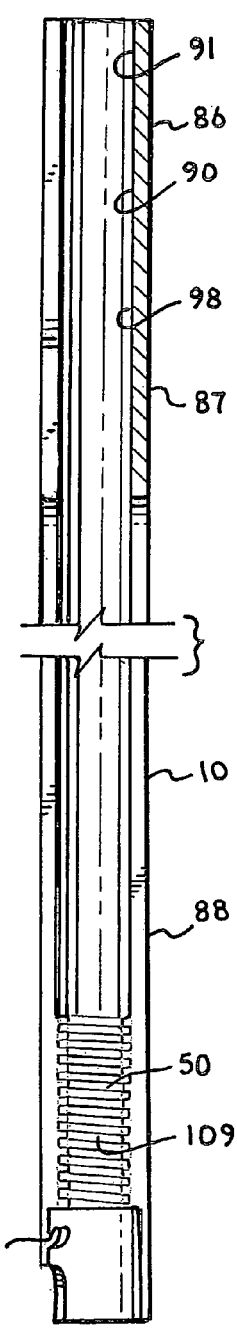

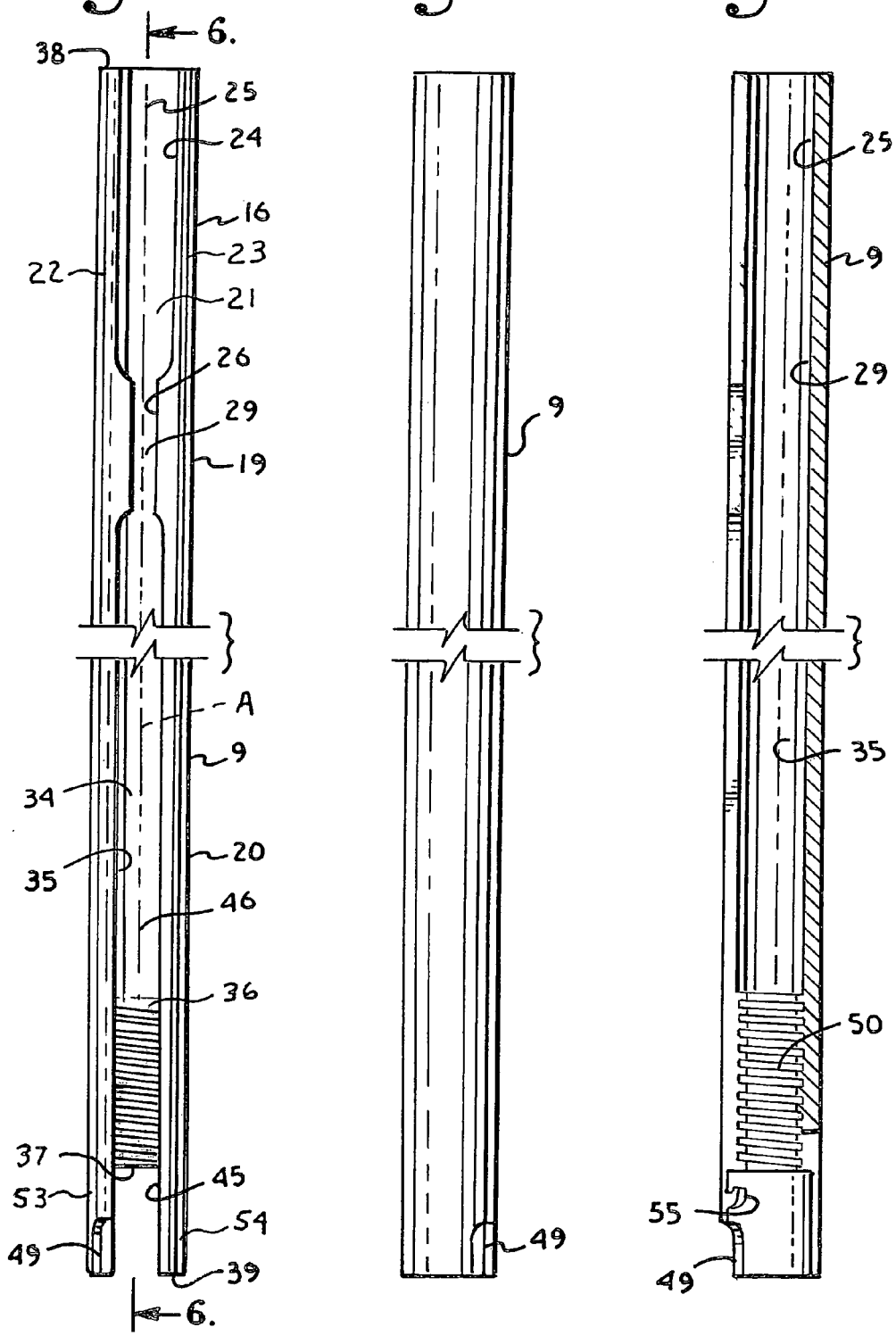

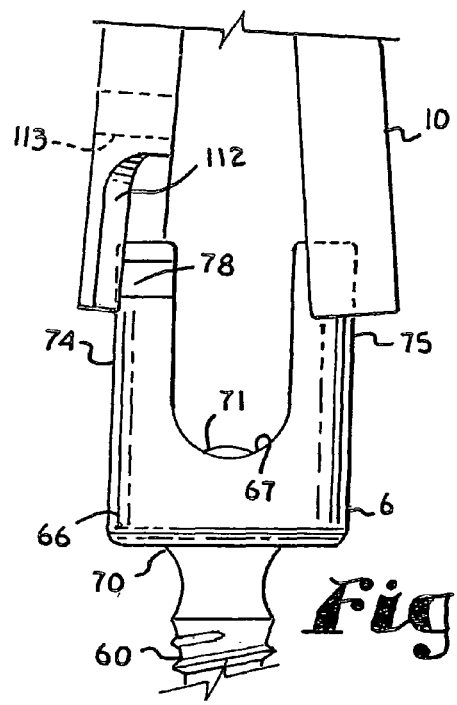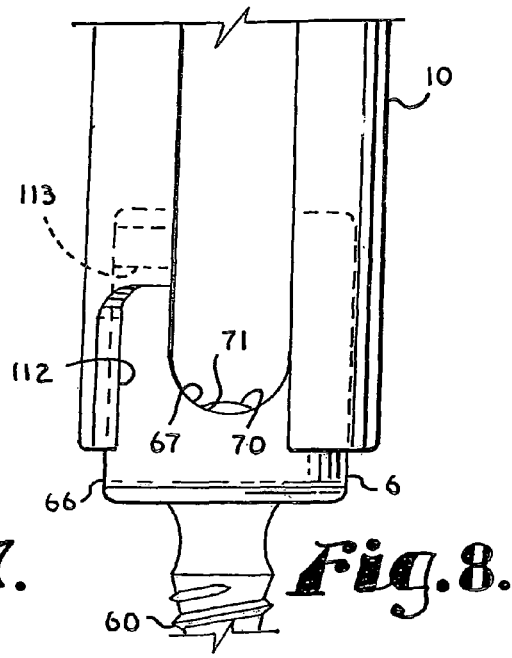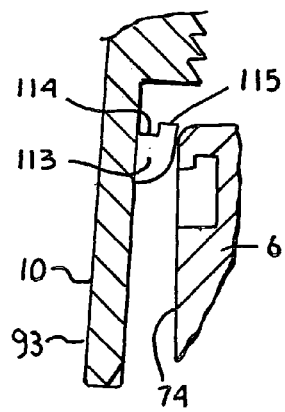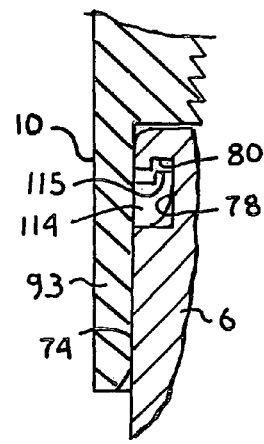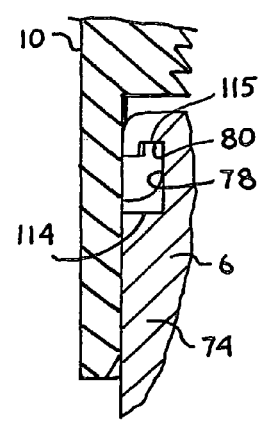

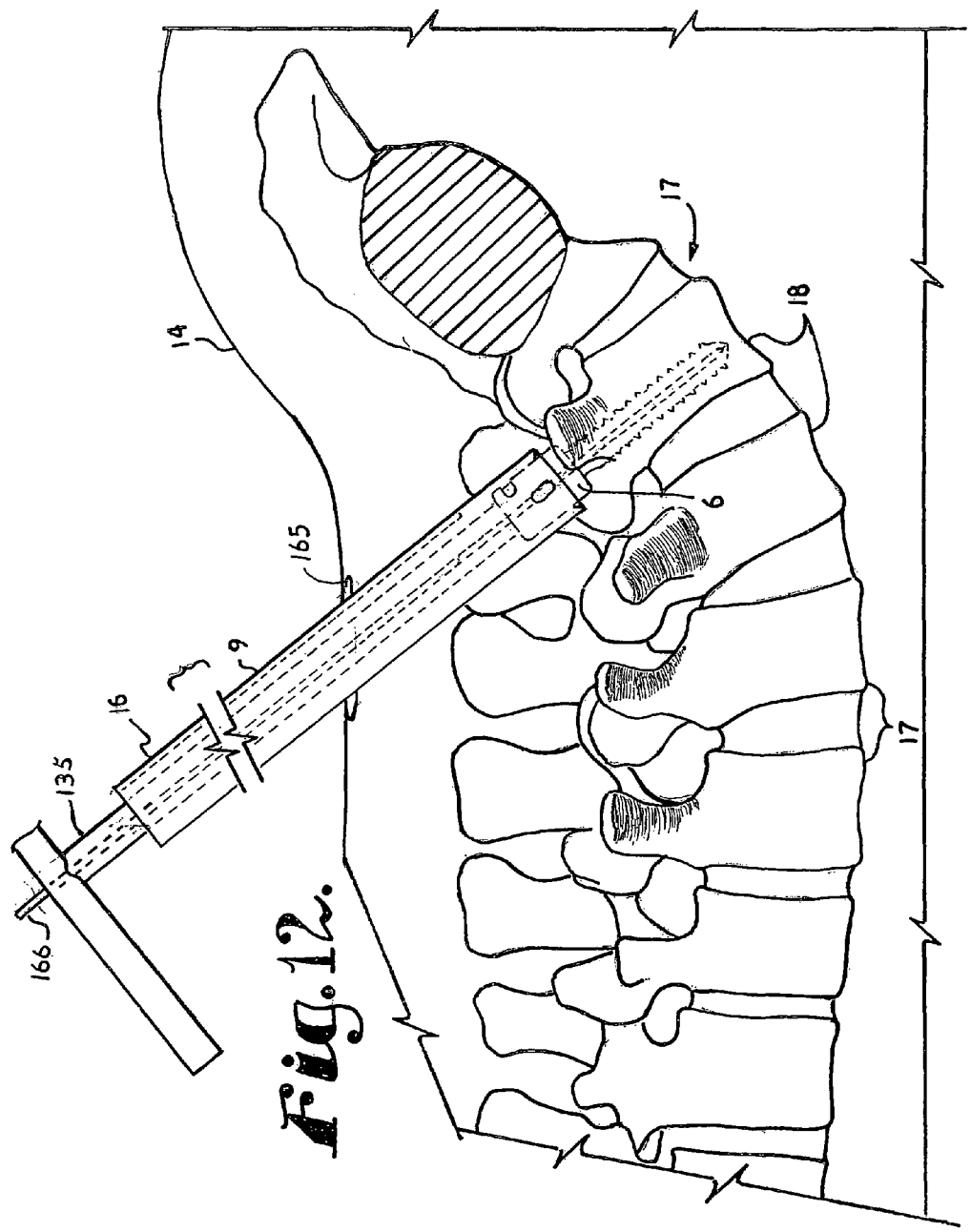

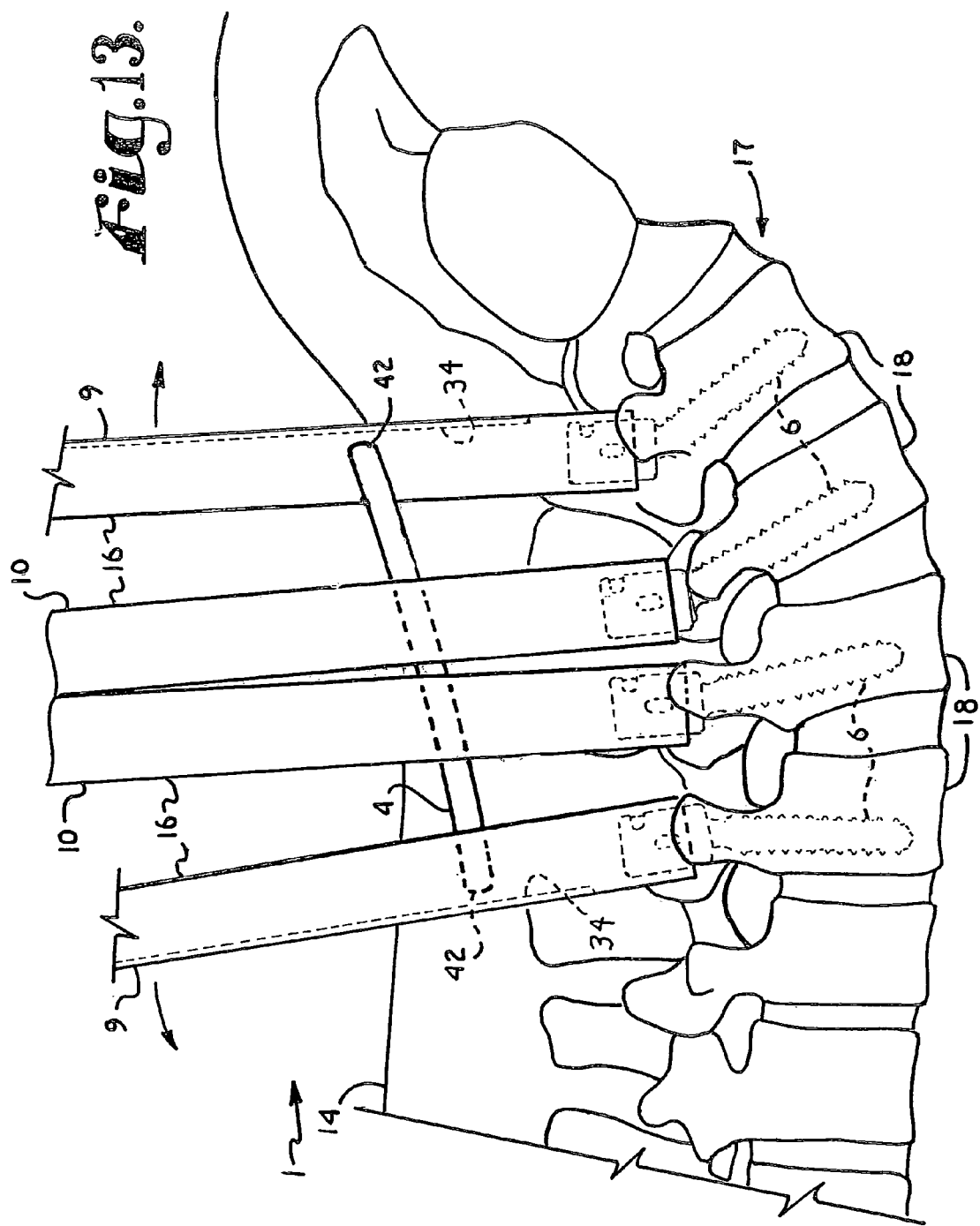

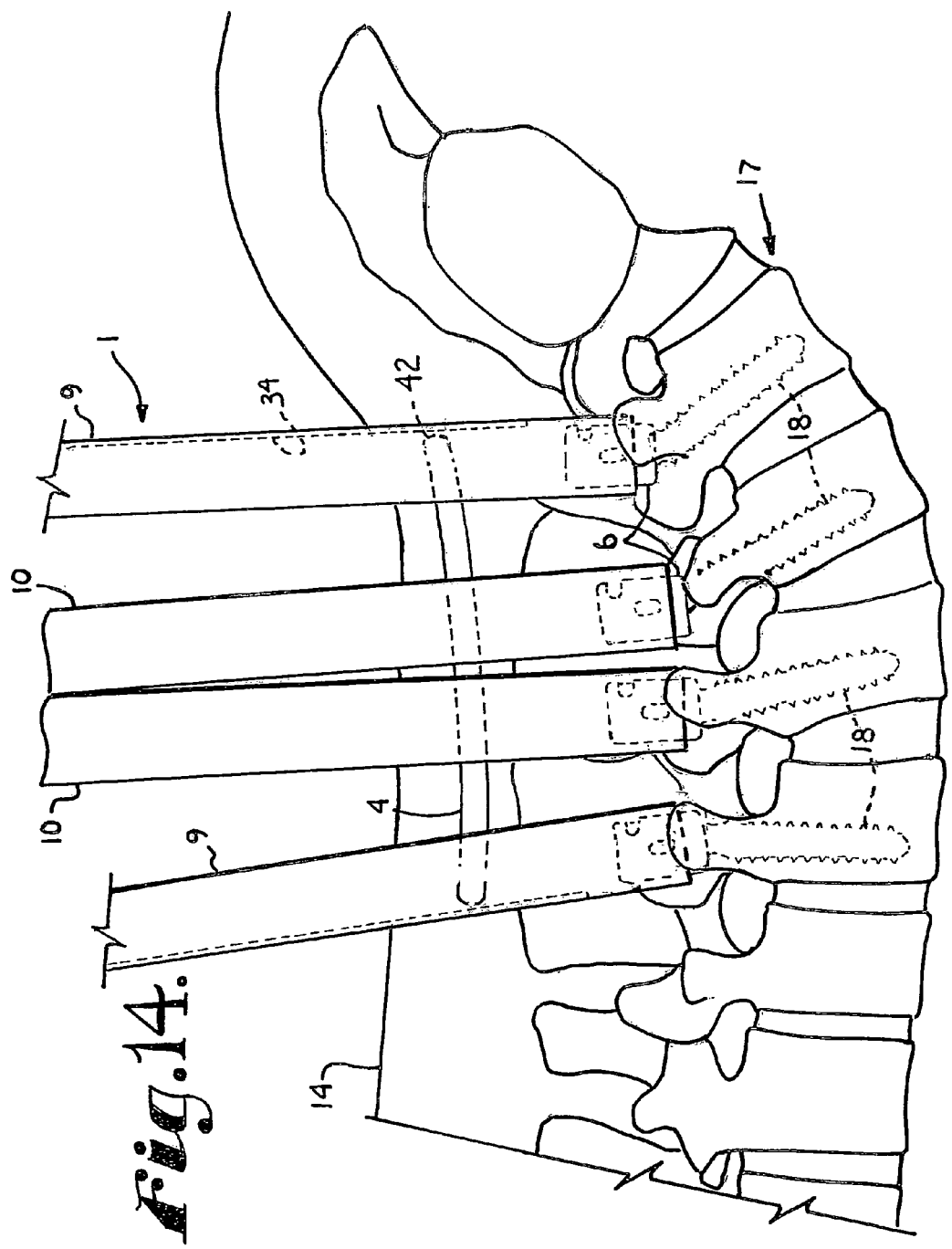

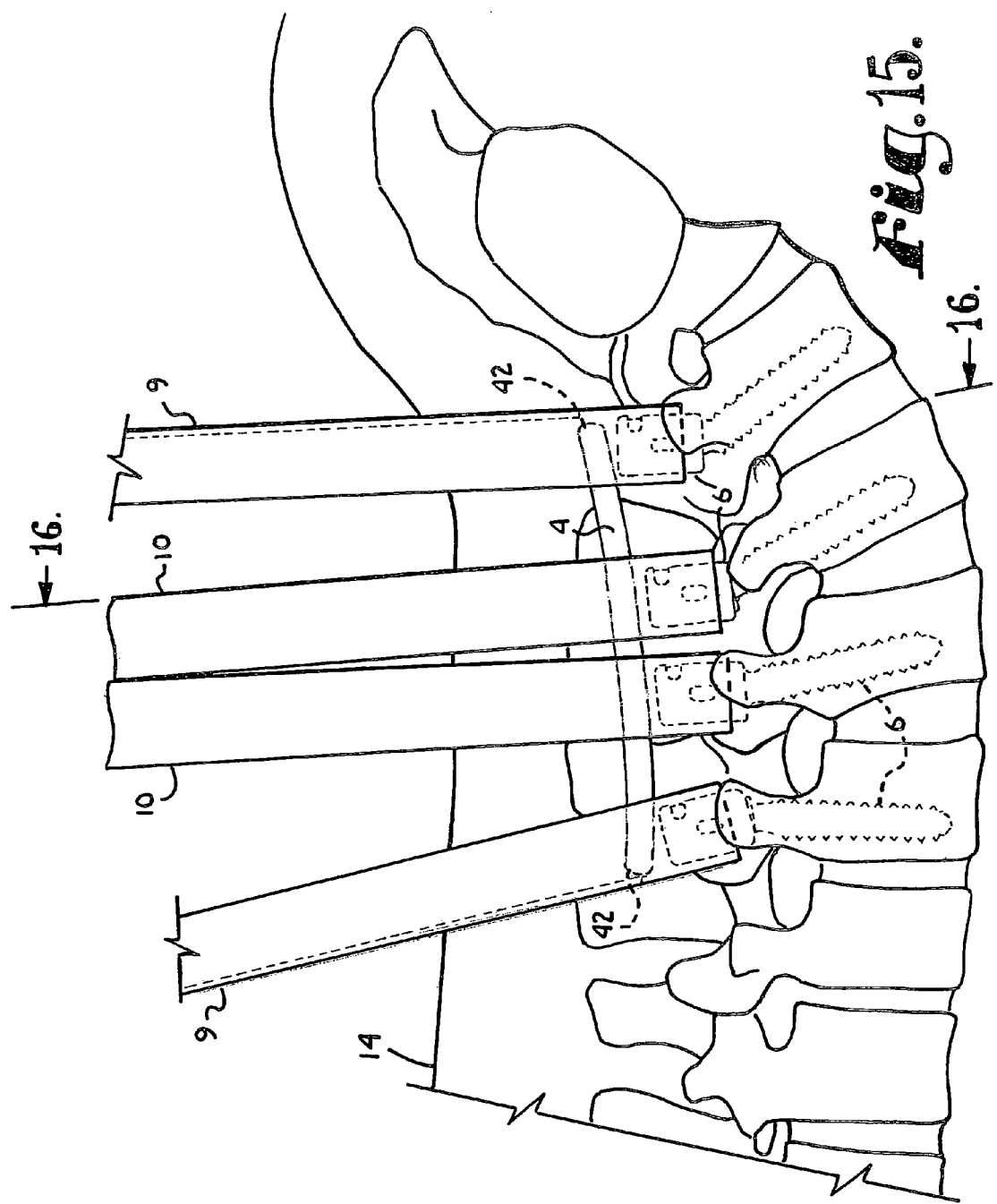

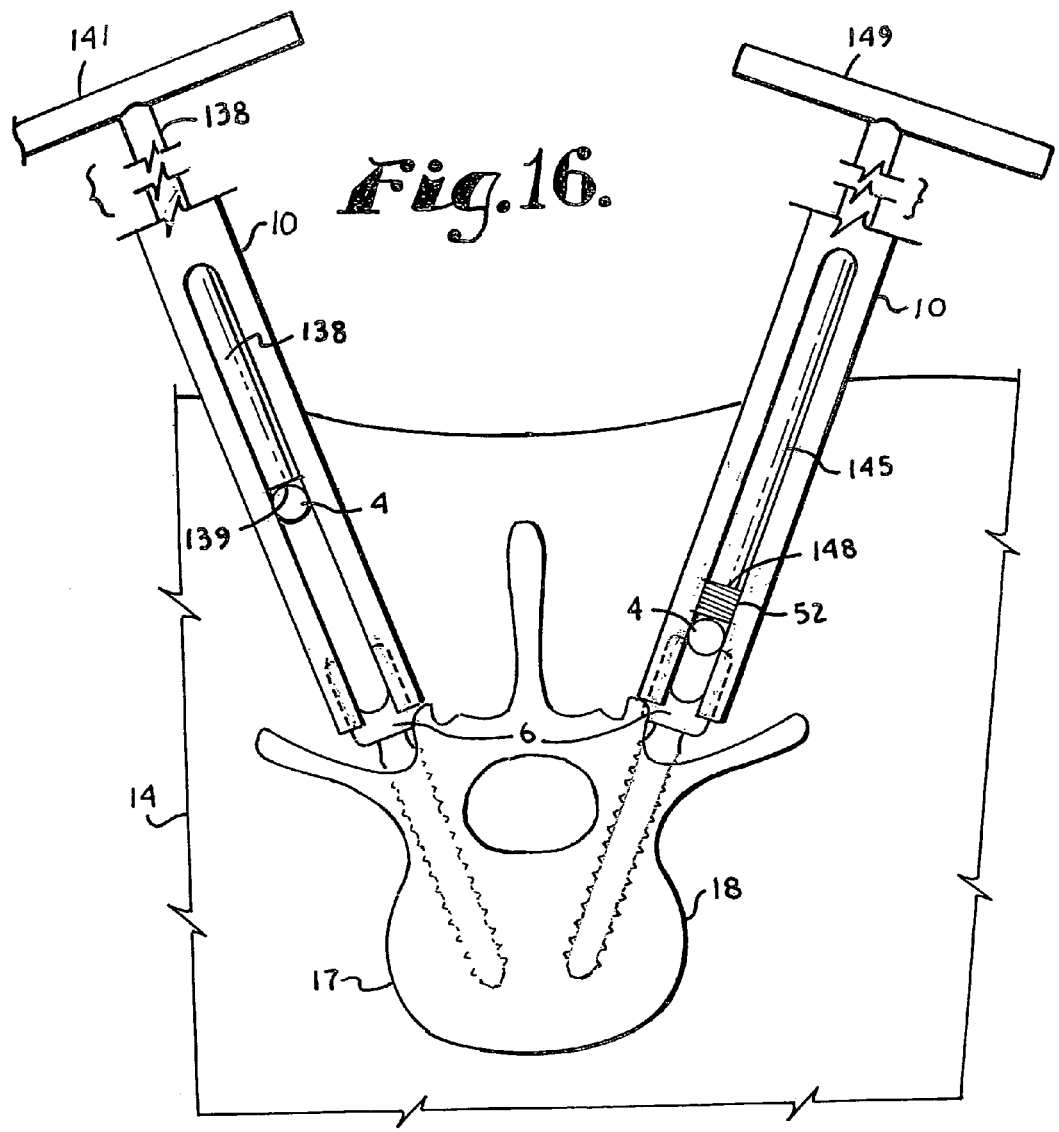

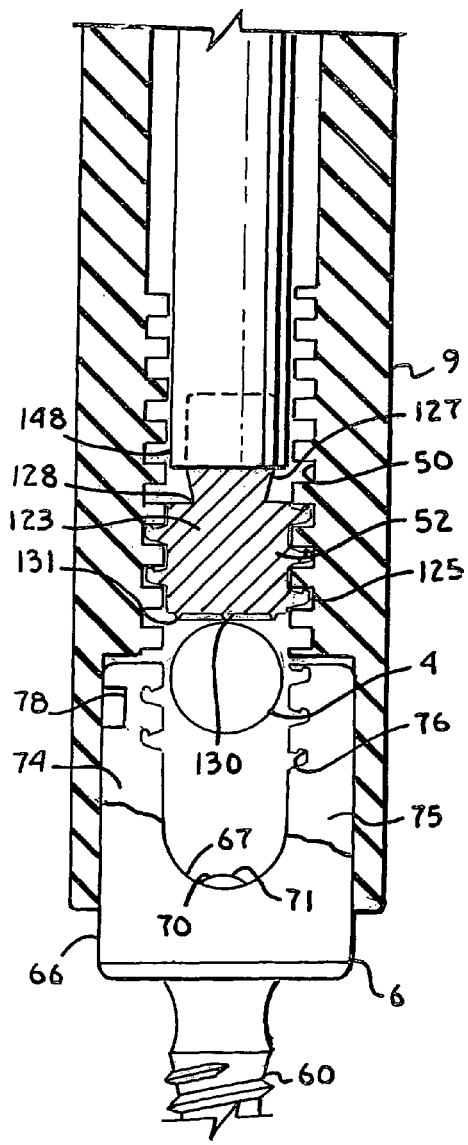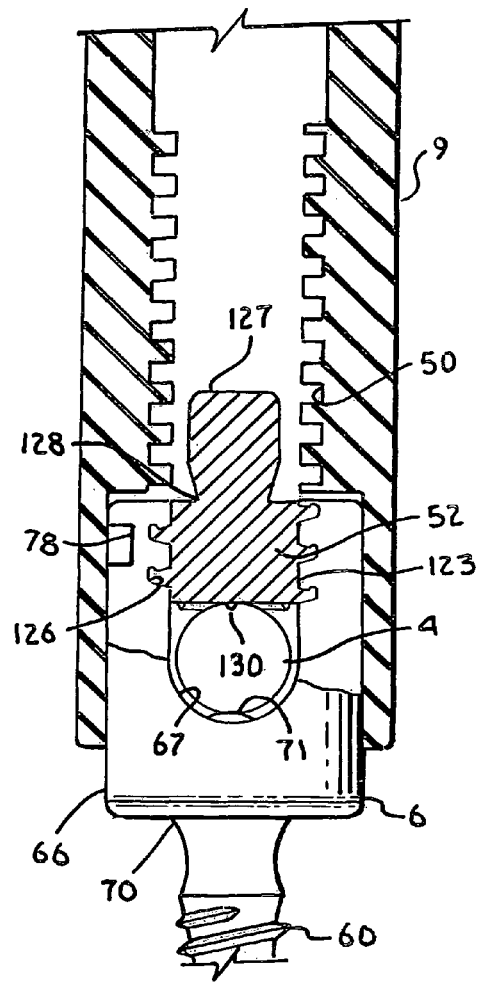

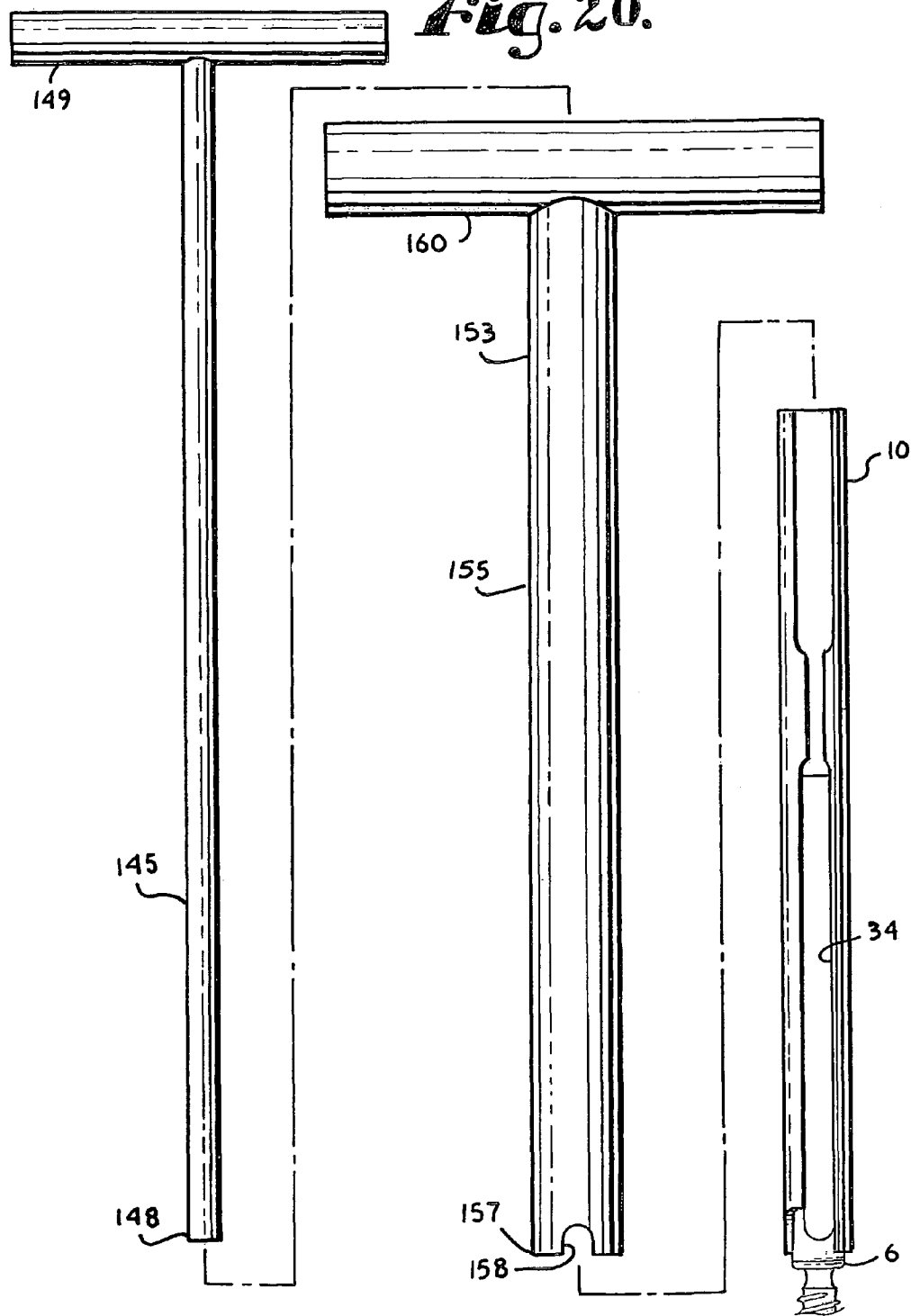

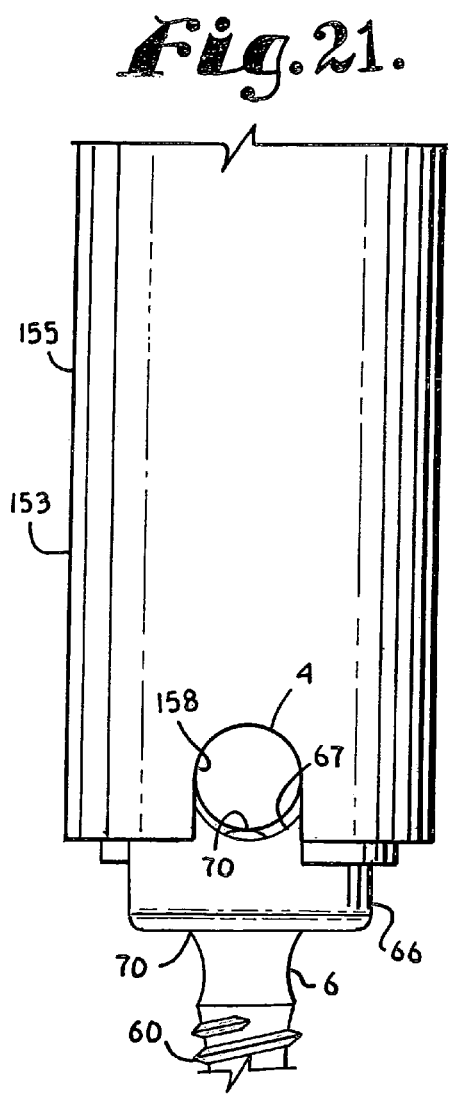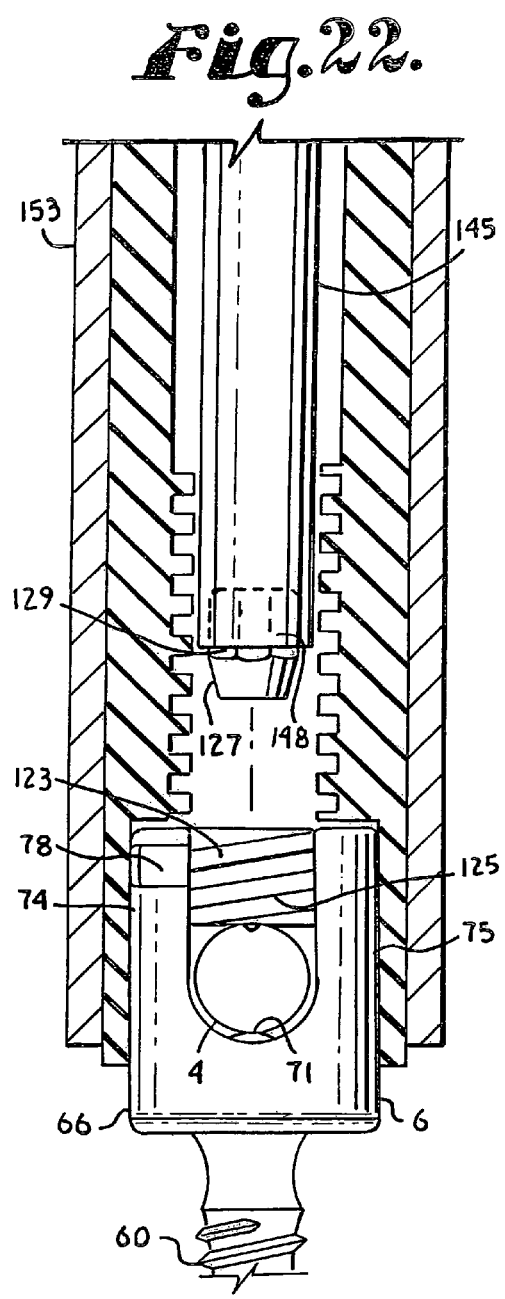

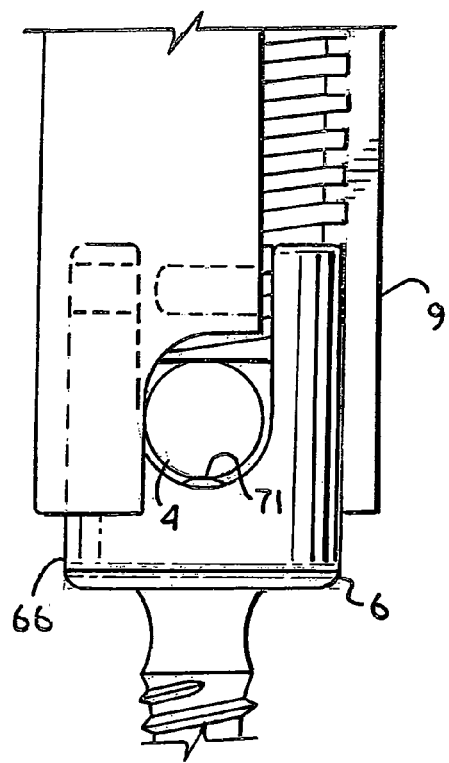
Fig.23.
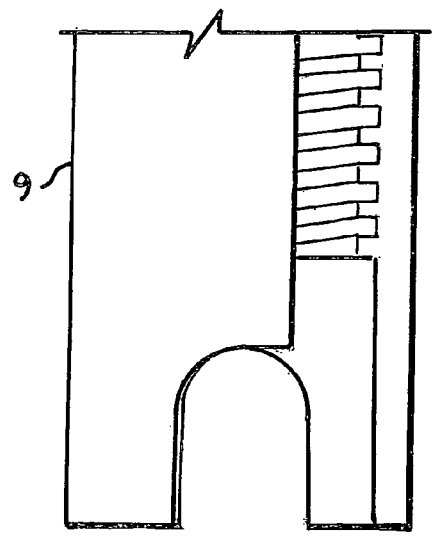
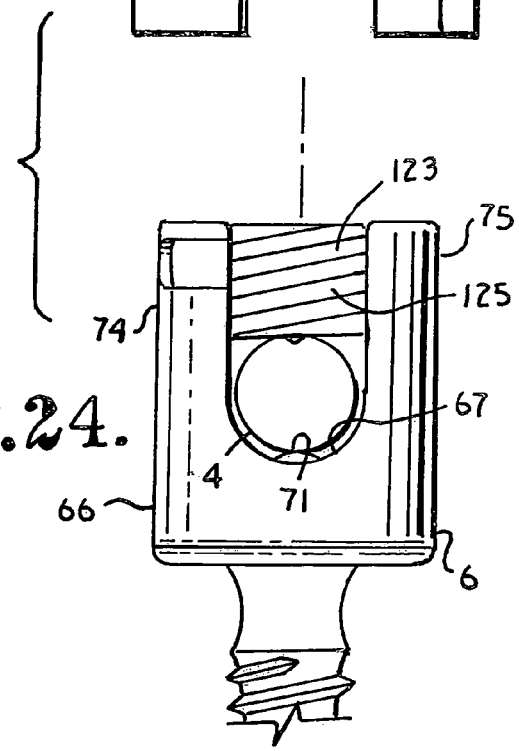
Fig.24.

ORTHOPEDIC IMPLANT ROD REDUCTION TOOL SET AND METHOD

CROSS-REFERENCE TO RELATED APPLICATION

This application is a continuation of U.S. patent application Ser. No. 12/584,413, filed Sep. 4, 2009, which as a continuation of U.S. patent application Ser. No. 12/220,185, filed Jul. 22, 2008, which is a Division of U.S. patent application Ser. No. 10/789,149, filed Feb. 27, 2004, which issued as U.S. Pat. No. 7,160,300 on Jan. 9, 2007, all of which are incorporated herein by reference.

BACKGROUND OF THE INVENTION

The present invention relates to apparatuses and methods for use in performing spinal surgery and, in particular, to tools and methods of using such tools, especially for percutaneously implanting a rod for spinal support and alignment using minimally invasive techniques.

For many years, spinal osteosynthesis apparatuses have been utilized to correct spinal deformities, injuries or disease. In such procedures, elongate rods are surgically attached to vertebrae of the spine to provide support and/or to reposition certain vertebrae. Such rods are secured to vertebrae utilizing bone screws and other implants.

Surgical techniques and bone screws have improved; however, in order to reduce the impact of such surgery on the patient, it has been desirable for such implants to be inserted percutaneously or with surgical techniques that are minimally invasive to the body of the patient. This presents a problem with implantation of rods that are elongate and have historically required a long incision and open wound in order to provide for the length of the rod and the space required for the surgeon's hands to manipulate the rod, implants and insertion tools used with the rod. Consequently, it has been desirable to develop apparatuses and techniques that allow for the insertion of bone screws, the insertion and reduction of a rod and the securing of the rod to the bone screws with significantly reduced invasion into the body of the patient and with minimal incision size in the skin over the operational site.

SUMMARY OF THE INVENTION

A set of tools is provided for percutaneously implanting a spinal rod in a patient. The tools include a pair of end guide tools that have channels sized to receive opposite ends of such a rod and allow sliding of the rod along the channel so as to guide ends of the rod into opposed end bone screw-heads to which the end guide tools are attached. Intermediate guide tools are also attached to bone screw-heads between the end bone screws and are slotted to guide the rod to respective bone screws attached to the intermediate guide tools.

The guide tools also include lower attachment structure to allow the guide tools to be easily and quickly secured to mating structure on a respective bone screw-head, and to be easily removed from the bone screw by manual rotation of a handle of the tools exterior of the patient, after which the guide tool is withdrawn from the patient. The intermediate guide tools have a snap-on and twist-off association with an associated intermediate bone screw and the end guide tools have a twist-on and twist-off association with respective end bone screws. In certain embodiments, other attachment structure may be used.

Each of the guide tools also includes an internal first lower guide and advancement structure that functions in cooperation with an internal second guide and advancement structure within the bone screw head and also with external helical wound thread or locking flange form mating structure on a bone screw closure top for closing the head of the bone screw, so as to be able to load the closure top though a top-to-bottom passageway in the guide tool and rotate the closure top with a closure top installation tool. Beneath the surface of the skin, the closure top is partially surrounded by the guide tool as it is directed to the bone screw. Clockwise rotation of the closure top in the region of the lower guide and advancement structure engages the closure top therewith and produces mechanical advantage that causes the closure top to be driven against the rod as it advances thereby urging the rod into the head of a respective bone screw. The closure top is driven and advanced by rotation of the closure top by the closure top installation tool and transferred or passed from the first guide and advancement structure in the guide tool to the second guide and advancement structure in the bone screw without losing mechanical advantage and while continually applying downward pressure on the rod, so as to drive the closure top downward and against the rod and so as to bias the rod into the head of the bone screw where it is captured by the closure top and locked in position.

OBJECTS AND ADVANTAGES OF THE INVENTION

Therefore, the objects of the present invention are: to provide a set of tools for implanting a spinal rod for support or alignment along a human spine with minimal surgical invasion of the patient; to provide such a set of tools including a pair of end tool guides for slidably guiding opposed ends of the rod toward end bone screws attached to the end guide tools; to provide such a set of tools including intermediate guide tools for each intermediate bone screw that guide the rod in slots therethrough to respective bone screws; to provide such a set of tools including rod pusher and closure top installation tools for assisting in securing the rod in the bone screws; to provide such a set of tools where the end guide tools include a longitudinal channel extending upwardly from near a bottom thereof to slidingly receive and guide ends of the rod toward associated end bone screws; to provide such a set of tools wherein the guide tools are easily attached to and disengaged from the bone screws; to provide such a set of tools wherein each guide tool includes a first guide and advancement structure near the bottom thereof that receives thread or locking flange mating structure on the closure top and advances the closure top upon rotation of the closure top to urge the rod downwardly; to provide such a set of tools wherein the guide tool first guide and advancement structure acts cooperatively with a second guide and advancement structure on the bone screw so as to transfer the closure top upon rotation thereof from the guide tool to the bone screw while continuously applying pressure to the rod and thereafter further advance the closure top to urge the rod into a seated position in the bone screw; to provide such a set of tools wherein the guide tools easily attach to and disengage from the bone screws by manual manipulation of the surgeon outside the patient's skin; to provide a method of implanting a rod into a patient with minimal surgical invasion of the patient; to provide such a method utilizing the previously described tools for percutaneous implantation of such a rod; to provide such a method wherein end guide tools are utilized to receive opposite ends of a rod and guide the rod ends in the guide tool channels through manipulation of the guide tools and use of rod pusher tools; to provide such a method wherein intermediate guide tools are utilized to guide intermediate locations along the rod to respective intermediate bone screws; to provide such a method wherein guide and advancement structure near the bottoms of the guide tools, on the bone screws and on the closure tops are utilized to pass the closure top under rotation and with driving force between the guide tools and the bone screws and to drive the rod into a seating position in the bone screw; and to provide such a set of tools and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary front elevational view of an intermediate guide tool in accordance with the present invention.

FIG. 2 is a fragmentary side elevational view of the intermediate guide tool.

FIG. 3 is a fragmentary cross sectional view of the intermediate guide tool, taken along line 3-3 of FIG. 1.

FIG. 4 is a fragmentary front elevational view of an end guide tool.

FIG. 5 is a fragmentary side elevational view of the end guide tool.

FIG. 6 is a cross sectional view of the end guide tool, taken along line 6-6 of FIG. 4.

FIG. 7 is an enlarged and fragmentary front elevational view showing snap-on installation of the intermediate guide tool on a polyaxial bone screw head.

FIG. 8 is an enlarged and fragmentary front elevational view showing the intermediate guide tool installed on the bone screw head.

FIG. 9 is a fragmentary and cross-sectional view showing an early stage of the snap on installation of the intermediate guide tool on the bone screw head.

FIG. 10 is a fragmentary and cross-sectional view showing a later stage of installation of the intermediate guide tool on the bone screw head.

FIG. 11 is a fragmentary and cross-sectional view showing the intermediate guide tool installed on the bone screw head.

FIG. 12 is a partial and generally schematic view of a patient's spine with the end guide tool in conjunction with a bone screw installation tool, at the end of a process of installing a bone screw with attached end guide tool in a spinal vertebra.

FIG. 13 is a partial and generally schematic view of the spine with a pair of end guide tools and a pair of intermediate guide tools mounted on respective implanted bone screws and being utilized in an early stage of rod implantation to guide the rod toward the bone screws.

FIG. 14 is a view similar to FIG. 13 showing an intermediate stage of guiding the rod toward the bone screws.

FIG. 15 is a view similar to FIG. 13 showing a later intermediate stage of guiding the rod toward the bone screws.

FIG. 16 is a partial and generally schematic cross sectional view of the spine showing rods being implanted on opposite sides of the spine and with the rod on the left in an early stage of implanting while the rod on the right is in a later stage of implanting, taken along line 16-16 of FIG. 15.

FIG. 17 is a cross-sectional view of an end guide tool, similar to FIG. 6, shown during installation of the rod and a closure top in the bone screw attached to the end guide tool.

FIG. 18 is a view similar to FIG. 17 showing the rod and closure top installed in the bone screw before final torquing of the closure top.

FIG. 20 is an exploded and front elevational view of a closure top installation tool, antitorque tool and one of the intermediate guide tools attached to a bone screw.

FIG. 21 is a fragmentary and front elevational view of the antitorque tool being positioned so as to allow final torquing to a closure top in the bone screw.

FIG. 22 is an enlarged and fragmentary side view of the end guide tool, as shown in FIG. 21, in conjunction with the installation tool and antitorque tool with portions broken away to shown interior detail and with the closure top having just been installed and torqued in the bone screw so that a break away head of the closure top has been removed.

FIG. 23 is a fragmentary and enlarged front elevational view showing an early stage in the removal of the end guide tool from the bone screw wherein the tool has been rotated approximately ninety degrees relative to its axis to the shown removal configuration from the installation configuration, such as seen in FIG. 17, thereof.

FIG. 24 is a fragmentary and enlarged front elevational view showing the end guide tool disengaged from the bone screw.

DETAILED DESCRIPTION OF THE INVENTION

Figure 19:
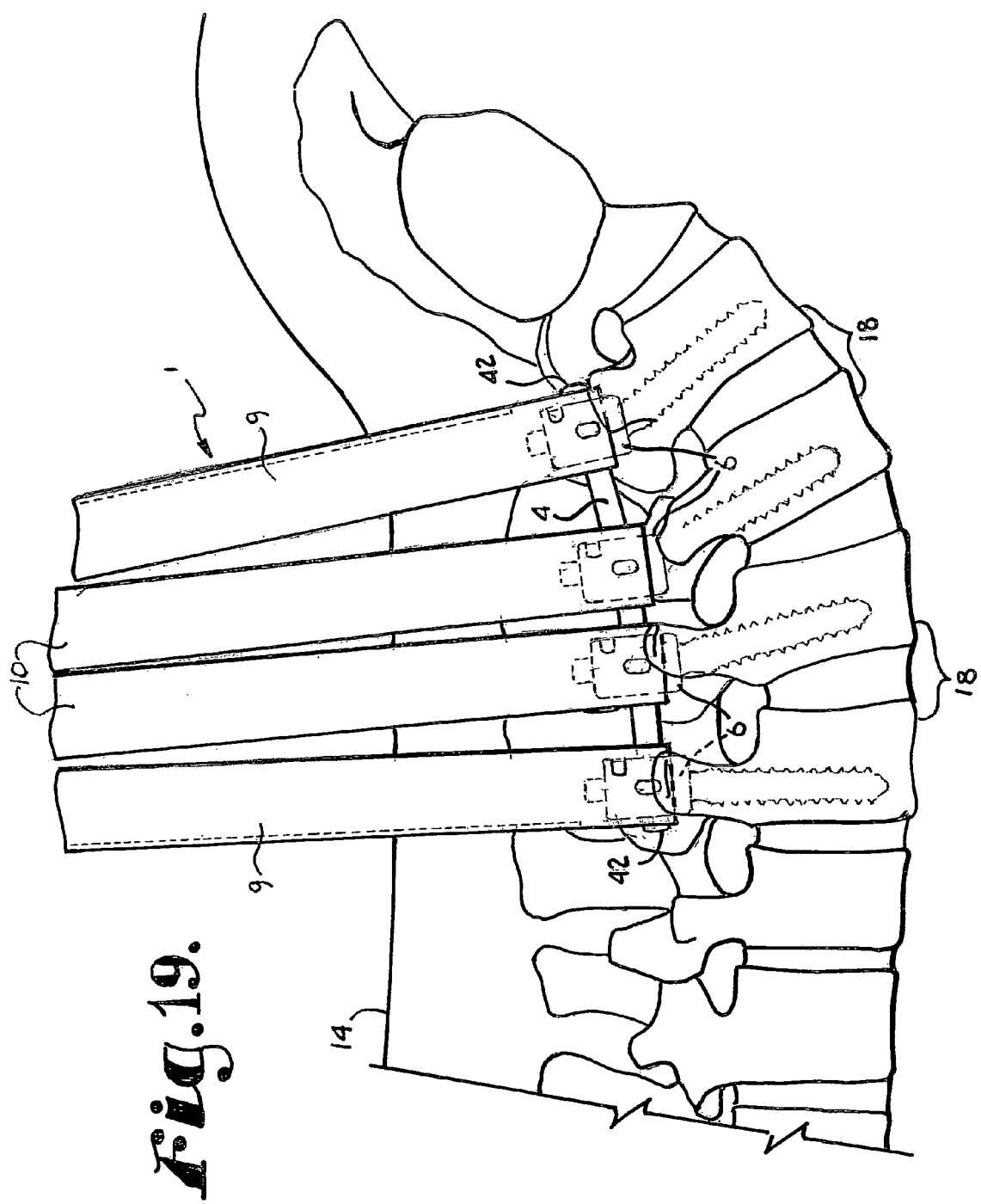
FIG. 19 is a partial and generally schematic side view of the spine showing the rod fully installed in the bone screws.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a tool set for use in installing an orthopedic spinal rod 4 into a set of bone screws 6 in accordance with the present invention.

The tool set 1 of the illustrated embodiment includes a pair of end guide tools 9 and a plurality of intermediate guide tools 10, which in the illustrated embodiment includes a pair of intermediate guide tools 10 on each side of a patient's spine 17, but which can include none, one or many intermediate guide tools 10 depending upon the particular application, so that one intermediate guide tool 10 is used for each intermediate bone screw 6 to which the rod 4 is to be attached. The bone screws 6 are implanted in the patent's spine 17 and, in particular, in vertebrae 18 along the spine 17. Rods 4 are often installed on both sides of the spine 17, as seen in FIG. 16, during the same procedure.

The end guide tool 9 is illustrated in FIGS. 4 through 6. In particular, each end guide tool 9 has an elongate body 14 that is sized and shaped to be sufficiently long to extend from implanted bone screws 6 through an exterior of a patient's skin 14 so as to provide an outwardly extending and upper handle portion 16 that allows and provides for gripping by a surgeon during procedures utilizing the tool set 1. Each of the end guides 9 include an intermediate portion 19 and a lower portion 20 along the length thereof. Each end guide tool 9 has a back wall 21 joining a pair of side walls 22 and 23.

More specifically, the upper portion 16 of each end guide tool 9 is generally channel shaped having a U-shaped cross-section, a C-shaped cross-section, a crescent shaped cross-section or the like in order to form an opening 24 that opens into and forms part of a channel 25 that opens radially to one side of the end guide tool 9 and defines the side to side opening 24 that is sufficiently wide to receive additional tools and/or a closure top, as will be discussed below. The intermediate portion 19 of each end guide also includes an outward facing channel 29 that has an opening 26 which is somewhat smaller than the opening 24 of the upper portion 16, such that the channel 29 is sized and shaped to receive certain tools, as described below. Finally, the end guide lower portion 20 also includes a groove or channel 34 opening radially outward and having a side-to-side width or opening 35 that is approximately the same size as the opening 26. The channel 34 has a rear web or wall 36 having a lower end 37. All of the channels 25, 29 and 34 communicate with one another and are aligned with one another so as to provide a continuous elongate interior passageway with an open side from near a top 38 to near a bottom 39 thereof. This passageway provides a continuous open path of non uniform cross-section radius from the top 38 to the bottom 39 thereof that is parallel to an elongate axis A of each end guide tool 9. As will be discussed later, each end guide tool channel 34 is especially sized and shaped to slidingly receive a respective end 42 of the rod 4 therein.

Near the end guide bottom 39 is a cut out 45 wherein a portion of the back wall 21 of the channel 34 is removed in order to provide a region having a size and shape to allow passage of a respective end 42 of the rod 4 therethrough. Also located near the end guide bottom 39 is a rod abutment recess 49 that is sized and shaped for the purpose of bridging the rod 4 when the end guide tool 9 is rotated for removal, as described below. The end guide tool 9 also receives a closure top 52, as will be described below. Still further, near the bottom 39 of each of the end guides 9 is a helical wound first guide and advancement structure 50 which may include conventional helical threads, helically wound square threads, or other guide and advancement structure to cooperate with equivalent or mateable structure within the bone screw heads 6 and on the closure top 52, as also described below. The lower free ends of the side walls 22 and 23 form spaced tangs or legs 53 and 54.

At the bottom 39 of each end guide tool 9 is a radially inward facing attachment structure 55 that includes a base 56 and an upperly and axially extending projection, flange or hook member 57 which will be described in conjunction with a bone screw 6 below.

Referring more specifically to the bone screw 6, each of the bone screws 6 includes a threaded shank 60 for screwing into and seating in a vertebra 18 that is part of the human spine 17, see FIG. 12. Each of the bone screws 6 also include a head 66 with a rod receiving channel 67 passing therethrough. Each of the bone screw shanks 60 includes an upper portion 70 that extends into the head 66 and is operationally secured therein, so that the head 66 is rotatable on the shank 60 until locked in position through engagement with the rod 4 under pressure. In particular, each shank upper portion 70 has an upwardly extending dome 71 that engages the rod 4, when the rod 4 is placed within an associated channel 67 so that as the rod 4 urges the dome 71 downwardly, the shank upper portion 70 frictionally locks the shank 60 in position in a fixed angular position relative to the head 66. Many different conventional bone screws where the head locks relative to the shank are well known in the art.

The present invention is not intended to be restricted to a particular type of bone screw. In the present embodiment, a polyaxial type bone screw 6 is utilized wherein the shank 60 is locked in position by direct contact with the rod 4. It is foreseen that tool set 1 of the present invention can be used with virtually any type of bone screw, including polyaxial bone screws of many different types wherein the head is locked relative to the shank by structure other than in the manner described in the illustrated embodiment.

Each bone screw head 66 has a pair of upstanding arms 74 and 75 with internal second guide and advancement structure 76 on the insides thereof. One of the arms 74 includes a circumferentionally located receiver 78 that comprises a lower slot 79 that extends partially circumferentially about the periphery of the arm 74 and ends in an upperwardly projecting but hidden recess 80. While the slot 79 is located on the arm 74 in the illustrated embodiment, a slot for this purpose could be located anywhere on the bone screw head 66. The slot 79 and recess 80 are sized, shaped and positioned so as to receive the attachment structure 55 of the end guides 9 therein. For greater detail, see the description below for the attachment structure associated with intermediate guide tools 10 and shown in FIGS. 10 and 11. The guide tool attachment structure 55 is sized and shaped to allow the attachment structure 55 to be received in the receiver 78 and locked therein by pulling the end guide tool 9 slightly axially upward relative to a respective bone screw 6. In order to disengage the guide tool 9 from the bone screw 6, the guide tool 9 is rotated 90 degrees counterclockwise from an attaching configuration, when viewing from the top so as to disengage the hook 57 from the recess 80 and so that the base 56 and hook 57 of the attachment structure 55 free to rotate above the rod 4 and closure top 52 and be released from the receiver 78. In this manner, end guide tools 9 twist off of respective bone screws 6 and in the particular illustrated embodiment the end guide tools 9 are also assembled on the bone screws 6 by the opposite twist on maneuver is the reverse of the twist off maneuver. In certain embodiments where there is enough flexibility in the legs 53 and 54, such that the legs 53 and 54 can be splayed radially outwardly at the bottom 39 thereof in the manner shown in FIG. 7, so the end guide tool 9 snaps-on over the bone screw 6, as will be described for the intermediate guide tools 10 below.

The unflexed space between the legs 53 and 54 that is equivalent to the width of the opening 35 is preferably substantially equivalent to the space between the bone screw arms 74 and 75 so that the channel 34 of the end guide tool 9 aligns with the channel 67 of the bone screw 6 when the end guide tool 9 is mounted on a respective bone screw 6. The recess 49 is sized, shaped and positioned so that when the rod 4 is located in the bone screws 6, the end guide tool 9 can rotate about axis A and the recess 49 allows the end guide tool 9 to straddle over the rod 4, thereby allowing the end guide tool 9 to twist relative to the bone screw 6 and free the attachment structure 55 from the receiver 78 and thereafter be removed after all procedures are complete, as described below.

Each of the intermediate guide tools 10 (see especially FIGS. 1 to 3) have a somewhat similar overall shape when compared to the end guide tools 9 in that both are preferably of the same axial length and width and also have much structure in common; however with certain differences as noted. Many of the structures of the intermediate guide tools 10 that are the same as the end guide tools 9 are given the same reference number and the above noted description applies to each such tool 9 or 10.

Each intermediate guide tool 10 has an overall elongate body 84 with an upper portion 86, an intermediate portion 87 and a lower portion 88. In the upper portion 86, the body 84 is generally C-shaped having a radially outward opening and elongate and axially extending channel 90 terminating in a web or rear wall 91 with side walls 92 and 93. The channel 90 has a front opening 95 that extends parallel to an axis of the body 84 and that is sized and shaped to receive tools and elements described below.

The intermediate portion 87 also includes an outwardly opening channel 97 with a rear web or wall 98 having a lower end 100 and a front opening 99 that is not as wide as the opening 95. The lower portion 88 includes two spaced side walls or legs 93 and 94 with an elongate and axially extending passthrough opening 101 between the legs 93 and 94 that extends more than halfway along the intermediate tool 10 and near the intermediate portion 87. The legs 93 and 94 define between them a pass through and aligned slot 105 sized and shaped to slidingly receive the rod 6.

The lower portion 88 extends substantially axially along the intermediate guide tools 10 and preferably to the location in use where the intermediate guide tools 10 pass through the skin 14.

The bottom 39 of each intermediate guide tool 10 includes a helically wound but discontinuous square thread or first guide and advancement structure 109 that cooperates with the closure top 52, as described below. The lower end of each intermediate guide tool 10 also includes a cutout 112 and an attachment structure 113 similar to structure 55 of the same type described for each end guide tool 9.

The attachment structure 113 (see especially FIGS. 9 to 11) includes a body 114 with an upperwardly extending, projection, flange or hook member 115 that follows the inner curvature of the guide tool leg 93. The body 114 extends radially inward and is sized and shaped to mate with and set within the bone screw head receiver 78. The bone screw receiver 78 is sufficiently wide to simultaneously receive both the body 114 and hook member 115 in a radially inward direction, as is shown in the view in FIG. 10. The attachment structure 113 is then set by axially raising the guide tool 10 relative to the bone screw 6 so at least part of the hook member 115 is located in the recess 80 which secures the guide tool 10 (likewise guide tool 9) to a respective bone screw 6, as seen in FIG. 11. This locks the guide tool 10 to a respective bone screw 6 and prevents outward splaying of the leg 93. This is a snap-on type installation or assembly as seen in FIG. 7 where the leg 93 splays outward during initial placement of the guide tool 10 over the bone screw 6 and then returns to an unsplayed position when the attachment structure 113 seats in the receiver 78, as shown in FIG. 10. Alternatively, the guide tool 10 can be rotated approximately 90° about its axis A prior to joining with a respective bone screw 6, the attachment structure 113 lowered through the opening between the bone screw arms 74 and 75 and aligned with the bone screw receiver 78, after which the guide tool 10 is rotated back to the first position shown in FIG. 11 in a twist on type assembly. In some instances the guide tool 10 is rotated somewhat more or less than ninety degrees to make the necessary alignment for removal which depends on the specific construction of the parts.

Enclosure 52 closes between the spaced bone screw arms 74 and 75 to secure the rod 4 in the channel 67. The closure top 52 can be any of many different plug type closures. Preferably the closure top 52 has a cylindrical body 123 that has a helically wound mating guide and advancement structure 125. The guide and advance at structure 125 can be of any type, including V-type threads, buttress threads, reverse angle threads, or square threads. Preferably the guide and advancement structure 125 is a helically wound flange form that interlocks with a reciprocal flange form as part of the second guide and advancement structure 76 on the interior of the bone screw arms 74 and 75. A suitable locking guide and advancement structure of this type is disclosed in U.S. Pat. No. 6,726,689 from Ser. No. 10/236,123 which is incorporated herein by reference. The helical wound guide 50 and advancement structure in the bottom 39 of each of the guide tools 9 and 10 is sized and shaped to receive the mating guide and advancement structure 125 of the closure top 52 and align with the second guide and advancement structure 76 of the bone screw 6 to form a generally continuous helically wound pathway, but does not require locking between the closure top 52 and the tools 9 and 10, even when a locking flange form is utilized on the closure top 52. The illustrated structure 125 has a square form or a square thread type shape. The guide 50 allows the closure top 52 to be rotated and the surgeon to develop mechanical advantage to urge or drive the rod 4, while still outside the bone screw head 6, toward and into the bone screw head 66. This is especially helpful where the rod 4 is bent relative to the location of the vertebra 18 to which the rod 4 is to attach and is not easily placed in the bone screw head 66 without force and the mechanical advantage provided by the guide 50. In particular, the first guide and advancement structure 109 on each tool 9 and 10 is located and positioned to align with the second guide and advancement structure 76 on the insides of the bone screw arms 74 and 75, as seen in FIGS. 17 and 18 and pass the closure top 52 therebetween while allowing the closure top 52 to continue to rotate and to continuously apply force to the rod 4, so as to seat the rod 4 in the bone screw head 66.

Each closure top 52 also preferably includes a break off head 127 that breaks from the body 123 in a break off region 128 upon the application of a preselected torque, such as 95 inch-pounds. The break off head preferably has a hexagonal cross section faceted exterior 129 that is adapted to mate with a similarly shaped socket of a closure driving or installation tool 145, described below. It is foreseen that different driving heads or other methods of driving the closure top 52 can be utilize with certain embodiments of the invention.

Additional tools are utilized to assemble the implant. In particular, FIG. 16 illustrates a rod pusher 136 on the left. The pusher 136 has an elongate shaft or rod 138 that is preferably received in and passes through the interior of the guides 9 and 10, such as the channel 90 of the guide tool 10. The pusher 136 also has a tip 139 for engaging and urging the rod 4 downward, where there is minor resistance, and a handle 141. It is foreseen that a pusher or gripper of the type that operates outside the guide tools 9 and 10 can be utilized, but is not preferred as such would normally require greater penetration of the skin 14 and more invasion of the patient.

Shown in FIG. 16 on the left and in FIG. 17 is the closure installation tool 145. The tool 145 has an elongate rod or shaft 147 adapted to be received in and pass axially through any of the channels of the guides 9 and 10 and a handle 149. The lower end of the rod 147 terminates in a socket 148 that is adapted to receive the closure break off head 127, as shown in FIG. 17.

Another tool used in implanting a rod 4 is an antitorque tool 153 which is seen in FIGS. 20 to 22. The antitorque tool 153 is preferably used with the closure installation tool 145 to torque and set the closure top 52, so it is snug against the rod 4, and thereafter break away the break off head 127 in the manner shown in FIG. 22. The antitorque tool 153 includes a tubular hollow shaft 155 that is sized and shaped to be slidably received over the guide 9 and 10. The antitorque tool 153 has a lower end 157 that has a pair of diametrically spaced bridges 158. Each of the bridges 158 is sized and shaped to fit over the rod 4, as seen in FIG. 21. When in place, as seen in FIG. 21, the antitorque tool 153 allows a surgeon to counter torque applied by the installation tool 145, when applying torque to and breaking away the break off head 127. The antitorque tool 153 also has an upper handle 16 with an opening through which the installation tool 145 passes in the manner suggested by the dashed lines in FIG. 20.

In use, the previously described tools are utilized to attach one or more rods 4 to the human spinal column 17.

The procedure is begun by forming a relatively small incision, such as incision 165 in the skin 14 for each bone screw 6 to be used. The incisions 165 are stretched into a round shape with a circumference equal to or just slightly larger than the guide tools 9 and 10. The skin 14 is relatively flexible and allows the surgeon to move the incision 165 around relative to the spine 17 to manipulate the various tools and implants, as required. A drill (not shown) is utilized to form a guide bore (not shown) in a vertebra 18 under guidance of non invasive imaging techniques, which procedure is well known and established. A thin pin 166 is inserted in the guide bore. A bone screw 6 is selected in accordance with the size of the patient's vertebra 18 and the requirements of the spinal support needed. Bone screws 6 having a rotatable or poly axial head 66 are preferred for the procedure, as such allow relatively easy adjustment of the rod 4 in the tools 9 and 10 during placement and for movement of tools 9 and 10, as described below. The bone screw 6 is also cannulated so as to be receivable over and guided by the pin 166 toward the proper position in the associated vertebra 18.

Before placing the bone screw 6 in the vertebra 18, the bone screw 6 is preferably joined to an associated guide tool 9 or 10. This could be done after insertion of the bone screw 6, but it is preferred to assemble both before inserting the bone screw 6. With respect to the intermediate guide tool 10, the lower end of the guide tool 10 is splayed or expanded outwardly by forcing the bone screw head 66 between the legs 93 and 94, in the manner shown in FIG. 7 until the attachment structure 113 aligns with the receiver 78 and the former snaps into the later, as shown in FIG. 8. Axial upward movement of the guide tool 10 relative to the bone screw 6 then sets the attachment structure 113 in the recess 80 in the process that is illustrated between FIGS. 10 and 11. Alternatively, the tool 10 can be axially rotated ninety degrees relative to the bone screw 6 and the attachment structure 113 aligned with the recess 80 and then rotated back. The placement of the guide tools 9 on the associated bone screws 6 normally follows the later twist on procedure, as the structure of the guide tools 9 allow less flexing because of the longer back wall 21. With tool 9, the attachment structure 55 is placed in a respective receiver 55.

A series of bone screws 6 are installed in each vertebra 18 to be attached to the rod 4 by use of a screwdriver or installation tool 135, see FIG. 12, that has a head, designed to grip the particular bone screw 6 used and which is also cannulated to receive the pin 166. For each bone screw 6, an associated guide tool 9 or 10 extends through the skin 14, as seen in FIG. 13. An end guide tool 9 is located at each end of the series of bone screws 6 and an intermediate guide tool 10 is located on each intermediate bone screw 6. The end guide tools 9 are turned or rotated so the channels 34 therein face one another and the intermediate guide tools 10 are aligned so slots 105 align with the channels 34.

The rod 4 is then inserted diagonally through one of the end skin incisions 165 in the manner shown in FIG. 13 so that a first rod end 42 passes through the slots 105 in any intermediate guide tools 10 and into the channel 34 of the opposed end guide tool 9. Back muscle tissue separates easily here to allow the upper insertion of the rod 4 and can be further separated by finger separation or cutting through one of the incisions 165, if required.

After initial insertion, the second end 42 of the rod 4 is positioned in the channel 34 of the end guide tool 9 that is located next to the insertion point of the rod 4, as is seen in FIG. 14.

Once the rod 4 is positioned in the guide tools 9 and 10, a pusher tool 136 of the type shown in FIG. 16 is utilized to push the rod 4 in each guide tool 9 or 10 toward the bone screw 6 associated with the guide tool 9 or 10 until the rod 4 is in approximately the position seen in FIG. 15. During this time, the end guide tools 9 can be manipulated to help movement of the rod 4 therealong and can especially have the tops thereof splayed outwardly relative to each other, as seen in FIG. 15. Again, the flexibility of the skin 14 allows such manipulation. Once the rod 4 reaches the bottom 39 of the end guide tools 9, the rod ends 42 encounter the cut outs 45 on either side of the rod 4 and pass therethrough. The rod 4 is sized to extend a little beyond each end bone screw 6 to ensure full capture and reduce likelihood of dislodgement. Because the channels 34 are slightly inward of the full outer length of the rod 4, the channels 34 must be tilted outward somewhat as seen in FIG. 15 to allow the rod 4 to pass down the channels 34 or one end 42 must be driven downward before the other. When the rod 4 is at the bottom of the guide tools 9 and 10, such as seen in FIG. 19, the end guide tools 9 can be returned to a position that is appropriate for properly aligning the bone screw heads 6 relative to the rod 4 prior to tightening and torquing the closure tops 52. Because the rod 4 is normally bent and/or the vertebrae 18 do not align properly, the rod 4 must normally be biased into the bone screw heads 6. This is accomplished by using the closure installation tool 145 in the manner illustrated on the right hand side in FIG. 16 and in FIG. 17.

In particular, the tool 145 has a socket 148 that grips the break off head 127 of the closure top 52. The installation tool 145 with closure top 52 therein is placed in the elongate top to bottom channel associated with the guide tools 9 and 10 either by entry from the side such as into channel 25 through opening 26 in guide tool 9 or into channel 25 through the top end 38 of the guide tool 9. The closure top 52 is then driven under manual control of the surgeon by use of the installation tool 145 toward the rod 4. Near the bottom of the guide tools 9 and 10, such as near the bottom 39 of end guide tool 9, the closure top 52 engages the helical wound first guide and advancement structure 50 and the tool 145 and closure top 52 are rotated mate the closure top helical mating structure 125 with the first guide and advancement structure 50 so as to drive the closure top 52 downward against the rod 4 and to urge the rod 4 downward into the bone screw channel 67. At the bottom of the guide tool 9 or 10, the closure top mating structure 125 engages and begins to mate with the guide and advancement structure 76 on a respective bone screw 6 and continued rotation of the tool 145 drives the rod 4 downward and into engagement with the dome 71 of the bone screw shank 60, so as to snug against and frictionally lock the shank 60 in position relative to the bone screw head 66, see FIG. 18.

Once all of the closure tops 52 are in final seating position in respective bone screws 6 and the surgeon is satisfied with the position of all of the elements, such as is seen in FIG. 19, the antitorque tool 153 is mounted over each guide tool 9 or 10, as shown in FIG. 21 with the bridges 158 straddling the rod 4 to prevent rotation. The installation tool 145 is inserted in the associated guide tool 9 or 10 and engaged with the break off head 127. By cooperative use of the tools 145 and 153 a preselected torque is manually applied to the break off head 127 and it breaks from the closure top body 123 in the manner shown in FIG. 22 and is removed along with the antitorque tool 153.

The guide tools 9 and 10 are then each rotated ninety degrees to align the attachment structure, such as structures 55 and 113 with the opening between bone screw arms 74 and 75, as shown in FIG. 23, so that the recess 49 straddles the rod 4 to allow the attachment structure 55 or 113 to disengage from the receiver 78. The guide tool 9 or 10 is then pulled axially upward away from the bone screw 6 and from the incision 165 in the skin 14, after which the incision 165 is closed.

It is to be understood that while certain forms of the present invention have been illustrated and described herein, it is not to be limited to the specific forms or arrangement of parts described and shown.

What is claimed and desired to be secured by Letters Patent is as follows:

1. A spinal bone screw implant in combination with a guide tool so that the tool attaches to the bone screw for guiding a rod into a receiver of the bone screw wherein:
 a) the receiver including a rod receiving channel and first attachment structure;
 b) the tool including a rod guide channel and a second attachment structure; the receiving channel and guide channel aligning during use to guide the rod from the tool to the receiver;
 c) the first attachment structure including a radiused horizontal groove extending at least partially circumferentially around the receiver, the tool having a projection that is sized and shaped to be received in the groove when the tool is secured to the receiver and to follow the groove upon rotation of the tool; and
 d) the tool including a cutout positioned to cooperate with the groove and sized, shaped and positioned to allow the tool, when the tool and receiver are joined, to straddle the rod when the tool is rotated so that the channels are not aligned so as to allow the projection to rotatably exit the groove and the tool to become unattached to the bone screw.

2. The combination of claim 1 wherein:
 a) the groove includes an upper recess; and
 b) the tool projection includes an upper hook member to mate with the recess when joined.

3. The combination of claim 1 wherein:
 a) the groove is sufficiently wide to receive the projection and hook member and thereafter the tool is pulled upwardly relative to the receiver to place the hook member in the recess so as to resist splaying of the tool relative to the receiver.

4. In a bone screw receiver adapted to join with a tool for use in conjunction with the receiver, the improvement wherein:
 a) the receiver includes an outward facing and at least partially circumferential horizontal groove adapted to receive a projection from the tool to secure the tool to the receiver and wherein the tool is rotated relative to the receiver so that the projection rotates relative to the groove for disconnecting the projection from the groove.

5. The receiver according to claim 4 wherein the groove includes an upper and inner recess adapted to receive a hook joined to the projection of the tool to resist splaying of the tool relative to the receiver during usage.

6. The receiver according to claim 4 wherein the receiver includes a channel for receiving a rod and in combination with the tool; and wherein the tool includes a lower cutout that is sized, shaped and positioned to straddle the rod when the tool is rotated to disengage the projection from the groove.

7. A combination of a bone screw receiver and a tool operably engaging the receiver in use; the receiver and tool having a common central longitudinal axis when joined; the receiver having a groove that is circumferentially and at least partially extending about an exterior of the receiver and that is radially positioned relative to the axis; the tool having a projection that is aligned and configured to be received in the groove when the tool engages the receiver; the tool being rotatable relative to the receiver so as to disengage the projection from the receiver and thereby release the tool from the receiver.

8. The combination according to claim 7 wherein the receiver has two upstanding arms forming a channel therebetween for receiving a rod and the tool has a pair of spaced legs with each of the legs engaging a respective arm, when joined.

9. The combination according to claim 8 wherein the legs are springy and join with the receiver by expanding outward and thereafter the projection that is located on one leg is received in the groove to secure the tool to the receiver.

10. The combination according to claim 8 wherein lower ends of the legs extend so as to be aligned with a rod in the channel when the tool and receiver are joined and wherein each leg includes a lower cutout that is sized, shaped and aligned to straddle the rod when the tool is rotated relative to the receiver to remove the tool from the receiver by disengaging the projection from the groove.

11. A guide tool for implanting a spinal rod in a patient wherein:
 a) the guide tool is non-integral with and adapted to be selectively and removably joinably attached at a lower end thereof to a spinal implant bone screw;
 b) the guide tool including a longitudinal channel between a pair of legs with a central axis and a central axial bore extending upwardly from said lower end thereof; said channel being sized and shaped so as to be adapted to receive the rod laterally positioned with respect to the axis of the channel for operably guiding the rod from a position exterior of the bone screw toward and into a receiver of the bone screw;
 c) a lower end of one of the legs having an inwardly projecting projection sized, shaped and positioned to be received in a circumferential outwardly facing groove on the receiver for holding the tool to the receiver and for allowing the tool to be removed from the receiver by rotation of the tool relative to the receiver so that the projection exits the groove.

12. The guide tool according to claim 11 in combination with the receiver.

13. A guide tool for implanting a spinal rod in a patient wherein:
 a) said guide tool having an inwardly directed projection at a lower end thereof and being non-integral with and adapted to be selectively and removably joinably attached at the projection to a groove in a receiver of a spinal implant bone screw receiver wherein the groove is circumferentially positioned on the receiver; and
 b) said guide tool including a central bore with a longitudinal axis, the bore extending along an entire length of the tool, and a side channel extending upwardly from said lower end thereof; said channel communicating with said bore and being sized and shaped and adapted to receive the rod laterally positioned with respect to the bore axis for operably guiding the rod from a position exterior of the bone screw toward and into the bone screw.

14. The tool of claim 13 in combination with the receiver.

* * * * *